(12) United States Patent
Adler et al.

(10) Patent No.: US 11,065,347 B2
(45) Date of Patent: Jul. 20, 2021

(54) METHODS FOR THE TREATMENT OF DANON DISEASE AND OTHER DISORDERS OF AUTOPHAGY

(71) Applicant: The Regents of the University of California, Oakland, CA (US)

(72) Inventors: Eric D. Adler, La Jolla, CA (US); Bradley Nelson, San Diego, CA (US); Sherin Hashem, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/070,233

(22) PCT Filed: Jan. 19, 2017

(86) PCT No.: PCT/US2017/014164
§ 371 (c)(1),
(2) Date: Jul. 13, 2018

(87) PCT Pub. No.: WO2017/127565
PCT Pub. Date: Jul. 27, 2017

(65) Prior Publication Data
US 2019/0054190 A1    Feb. 21, 2019

Related U.S. Application Data

(60) Provisional application No. 62/280,269, filed on Jan. 19, 2016.

(51) Int. Cl.
| | | |
|---|---|---|
| *A01N 63/00* | (2020.01) | |
| *A61K 48/00* | (2006.01) | |
| *C07K 14/705* | (2006.01) | |
| *C12N 15/86* | (2006.01) | |
| *C12N 15/864* | (2006.01) | |
| *A61P 3/00* | (2006.01) | |
| *A61P 9/00* | (2006.01) | |
| *A61K 9/00* | (2006.01) | |

(52) U.S. Cl.
CPC .......... *A61K 48/005* (2013.01); *A61K 9/0019* (2013.01); *A61P 3/00* (2018.01); *A61P 9/00* (2018.01); *C07K 14/70596* (2013.01); *C12N 15/86* (2013.01); *C12N 15/8645* (2013.01); *A01K 2217/075* (2013.01); *A01K 2227/105* (2013.01); *A01K 2267/0306* (2013.01); *C12N 2750/14143* (2013.01)

(58) Field of Classification Search
CPC ...... A61K 48/005; C12N 15/8645; A61P 9/00
USPC ............... 514/44; 424/93.1, 93.2; 435/320.1
See application file for complete search history.

(56) References Cited

U.S. PATENT DOCUMENTS

| | | | |
|---|---|---|---|
| 5,139,941 A | 8/1992 | Muzycka et al. | |
| 5,173,414 A | 12/1992 | Lebkowski et al. | |
| 8,796,236 B2* | 8/2014 | Dodge ................... | C12N 15/86 |
| | | | 514/44 R |
| 2004/0053870 A1 | 3/2004 | Yew et al. | |
| 2010/0183577 A1 | 7/2010 | Stern et al. | |
| 2010/0284990 A1 | 11/2010 | Kaemmerer et al. | |
| 2013/0184223 A1 | 7/2013 | Land et al. | |
| 2014/0112896 A1* | 4/2014 | Rebar ..................... | A61K 38/46 |
| | | | 424/93.21 |
| 2014/0225896 A1 | 4/2014 | Rebar | |
| 2015/0273016 A1 | 10/2015 | Parenti et al. | |
| 2016/0060656 A1 | 3/2016 | Rebar | |
| 2019/0054190 A1 | 2/2019 | Adler et al. | |

FOREIGN PATENT DOCUMENTS

| | | |
|---|---|---|
| WO | 1993/03769 | 1/1992 |
| WO | 1992/001070 | 3/1993 |
| WO | 2004/048537 | 6/2004 |
| WO | 2017/127565 | 7/2017 |

OTHER PUBLICATIONS

Su (Brain Res., 2016, vol. 1644, p. 98-106).*
Sun (Mol. Ther. 2003, vol. 7, p. 193-201).*
D'Souza (Circ. Heart Failure, 2014, vol. 7, p. 843-849).*
Franco (Mol. Therapy, 2005, vol. 12, No. 5, p. 876-884).*
Chandler (Human Mol. Genetics, 2017, available online 10-25016, vol. 27, No. 1, p. 52-64).*
Adler (JACC, Mar. 12, 2019, vol. 73, No. 9, 1 page).*
Fu (Mol. Therapy, 2011, vol. 19, No. 6, p. 1025-1033).*
Strausberg (GenBank BC002965, 2002).*
Weismann (Human Mol. Genetics, 2015, vol. 24, No. 15, p. 4353-4364).*
Jackson (Front. Mol. Neurosci., 2016, vol. 9, Article 116).*
Gray (Mol. Therapy, 2011, vol. 19, No. 6, p. 1058-1069).*
Inagaki (Mol. Therapy, 2006, vol. 14, No. 1, p. 45-53).*
Ruzo (Human Gene THeapry, 2012, vol. 23, No. 12, p. 1237-1246).*
Endo (Acta Neuropathol. 2015, vol. 129, p. 391-398).*
Xu (Gene, 2001, vol. 272, p. 149-156).*
Adler, E. et al. (2019). "AAV9.LAMP-2B improves metabolic and physiologic function in murine and human in-vitro models of Danon disease," JACC, Mar. 12, 2019, vol. 73, Issue 9, 1 total page.
Brown, H.C. et al. (2018). "Target-cell directed bioengineering approaches for gene therapy of Hemophilia A," Mol. Ther. Methods Clin. Dev. 9:57-69.

(Continued)

*Primary Examiner* — Michael C Wilson
(74) *Attorney, Agent, or Firm* — K&L Gates LLP; Louis C. Cullman; David Diamond

(57) ABSTRACT

This disclosure provides gene therapy vectors comprising a polynucleotide encoding one or more isoforms of lysosome-associated membrane protein 2 (LAMP-2), and methods of using such gene therapy vectors for the treatment of Danon disease and other autophagy disorders.

14 Claims, 19 Drawing Sheets

Specification includes a Sequence Listing.

(56) References Cited

OTHER PUBLICATIONS

Chandler, R.J. et al. (2017). Systemic AAV9 gene therapy improves the lifespan of mice with Niemann-Pick disease, type C1, Human Mol. Genetics 27:52-64.
Cuervo, A.M. et al. (2000). "Unique properties of lamp2a compared to other lamp2 isoforms," Journal of Cell Science 113:4441-4450.
D'Souza, R.S. et al. (2014). "Danon Disease—Clinical features, evaluation, and management," Circ. Heart Failure 7:843-849.
Extended European Search Report dated Jul. 26, 2019, for EP application No. 17 741 940.5, filed on Jan. 19, 2017, 5 pages.
Franco, L.M. et al. (2005). "Evasion of immune response to introduced human acid α-Glucosidase by liver-restricted expression in Glycogen storage disease Type II," Mol. Therapy 12:876-884.
Ioannou Y.A et al. (2003). "Gene Therapy for Lysosomal Storage Disorders," Expert Opin. Biol. Ther. 3:789-801.
International Search Report dated Apr. 4, 2017, for PCT application No. PCT/US2017/014164, filed on Jan. 19, 2017, 4 pages.
Su, C. et al. (2016). "Geniposide reduces α-synuclein by blocking microRNA-21/lysosome-associated membrane protein 2A interaction in Parkinson disease models," Brain Res. 1644:98-106.
Sun, B-D. et al. (2003). "Long-term correction of glycogen storage disease type II with a hybrid Ad-AAV vector," Mol. Ther. 7:193-201.
Written Opinion of the International Searching Authority dated Apr. 4, 2017, for PCT application No. PCT/US2017/014164, filed on Jan. 19, 2017, 5 pages.
Zhou, D. et al. (2005). "Lamp-2a Facilitates MHC Class II Presentation of Cytoplasmic Antigens," Immunity 22:571-581.
Cearley, C. et al. (2008). Expanded Repertoire of AV Vector Serotypes Mediate Unique Patterns of Transduction in Moue Brain, Molecular Therapy 16(10):1710-1718.
Hashem, S, et al. (2015). Oxidative stress Mediates Cardiomyocyte Apoptosis in a Human Model of Danan Disease and Heart Failure, Stem Cells 33(7):2343-50.
Stypmann J. et al. (2006) LAMP-2 deficient mice show depressed cardiac contractile function without significant changes in calcium handling, Basic Res Cardiol. 101(4):281-91.
Nishino, I. et al. (2000) Primary LAMP-2 deficiency causes X-linked vacuolar cardiomyopathy and myopathy (Danon disease), Nature 406(6798):902-6.
Powell, et al., Viral Expression Cassette Elements to Enhance Transgene Target Specificity and Expression in Gene Therapy, Discov Med 19(102):49-57, 2015.

* cited by examiner

Figure 1A

| ITR | Promoter | LAMP-2 (A, B, C) | 3' UTR | Poly A | ITR |

Figure 1B

| ITR | CAG Promoter | CBA Intron | LAMP-2 (A, B, C) | WPRE | RBG | ITR |

Figure 1C

| ITR | Native LAMP-2 Promoter | LAMP-2 (A, B, C) | 3' UTR | Poly A | ITR |

Figure 1D

| ITR | EF-1 Alpha Promoter | LAMP-2 (A, B, C) | 3' UTR | Poly A | ITR |

Figure 1E

| ITR | Cardiac-specific Promoter | LAMP-2 (A, B, C) | 3' UTR | Poly A | ITR |

Figure 1F

| ITR | Muscle-specific Promoter | LAMP-2 (A, B, C) | 3' UTR | Poly A | ITR |

Figure 1G

| ITR | Promoter 1 | LAMP-2 (A, B, C)/3' UTR/Poly A | Promoter 2 | LAMP-2 (A, B, C)/3' UTR/Poly A | ITR |

Figure 1H

| ITR | Promoter 1 | (+) LAMP-2 (A, B, C)/3' UTR/Poly A | (-) LAMP-2 (A, B, C)/3' UTR/Poly A | Promoter 2 | ITR |

Figure 1I

| ITR | Promoter | LAMP-2 (A, B, C) | IRES | LAMP-2 (A, B, C) | 3'UTR | Poly A | ITR |

Figure 1J

| ITR | Promoter | LAMP-2 (A, B, C) | P2A | LAMP-2 (A, B, C) | 3'UTR | Poly A | ITR |

Figure 1K

| ITR | Promoter | LAMP-2 Exons 1-8 | Intron | LAMP-2 (A, B, C) Exon 9/3'UTR/Poly A | Intron | LAMP-2 (A, B, C) Exon 9/3'UTR/Poly A | ITR |

Figure 1L

| ITR | Promoter 1 | LAMP-2 (A, B, C)/3' UTR/Poly A | Promoter 2 | LAMP-2 (A, B, C)/3' UTR/Poly A | Promoter 3 | LAMP-2 (A, B, C)/3' UTR/Poly A | ITR |

Figure 1M

| ITR | Promoter | LAMP-2 (A, B, C) | IRES | LAMP-2 (A, B, C) | IRES | LAMP-2 (A, B, C) | 3' UTR | Poly A | ITR |

Figure 1N

| ITR | Promoter | LAMP-2 (A, B, C) | P2A | LAMP-2 (A, B, C) | P2A | LAMP-2 (A, B, C) | 3' UTR | Poly A | ITR |

Figure 1O

| ITR | Promoter | LAMP-2 Exons 1-8 | Intron | LAMP-2B Exon 9/3' UTR/Poly A | Intron | LAMP-2A Exon 9/3' UTR/Poly A | Intron | LAMP-2C Exon 9/3' UTR/Poly A | ITR |

Figure 3A

*LAMP-2A* coding sequence (human) (SEQ ID NO:1)

ATGGTGTGCTTCCGCCTCTTCCCGGTTCCGGGCTCAGGGCTCGTTCTGGTCTGCCTA
GTCCTGGGAGCTGTGCGGTCTTATGCATTGGAACTTAATTTGACAGATTCAGAAAAT
GCCACTTGCCTTTATGCAAAATGGCAGATGAATTTCACAGTTCGCTATGAAACTACA
AATAAAACTTATAAAACTGTAACCATTTCAGACCATGGCACTGTGACATATAATGGA
AGCATTTGTGGGGATGATCAGAATGGTCCCAAAATAGCAGTGCAGTTCGGACCTGGC
TTTTCCTGGATTGCGAATTTTACCAAGGCAGCATCTACTTATTCAATTGACAGCGTC
TCATTTTCCTACAACACTGGTGATAACACAACATTTCCTGATGCTGAAGATAAAGGA
ATTCTTACTGTTGATGAACTTTTGGCCATCAGAATTCCATTGAATGACCTTTTTAGA
TGCAATAGTTTATCAACTTTGGAAAAGAATGATGTTGTCCAACACTACTGGGATGTT
CTTGTACAAGCTTTTGTCCAAAATGGCACAGTGAGCACAAATGAGTTCCTGTGTGAT
AAAGACAAAACTTCAACAGTGGCACCCACCATACACACCACTGTGCCATCTCCTACT
ACAACACCTACTCCAAAGGAAAAACCAGAAGCTGGAACCTATTCAGTTAATAATGGC
AATGATACTTGTCTGCTGGCTACCATGGGGCTGCAGCTGAACATCACTCAGGATAAG
GTTGCTTCAGTTATTAACATCAACCCCAATACAACTCACTCCACAGGCAGCTGCCGT
TCTCACACTGCTCTACTTAGACTCAATAGCAGCACCATTAAGTATCTAGACTTTGTC
TTTGCTGTGAAAAATGAAAACCGATTTTATCTGAAGGAAGTGAACATCAGCATGTAT
TTGGTTAATGGCTCCGTTTTCAGCATTGCAAATAACAATCTCAGCTACTGGGATGCC
CCCCTGGGAAGTTCTTATATGTGCAACAAAGAGCAGACTGTTTCAGTGTCTGGAGCA
TTTCAGATAAATACCTTTGATCTAAGGGTTCAGCCTTTCAATGTGACACAAGGAAAG
TATTCTACAGCTCAAGACTGCAGTGCAGATGACGACAACTTCCTAGTGCCCATAGCG
GTGGGAGCTGCCTTGGCAGGAGTACTTATTCTAGTGTTGCTGGCTTATTTTATTGGT
CTCAAGCACCATCATGCTGGATATGAGCAATTTTAG

Figure 3B

LAMP-2A protein sequence (human) (SEQ ID NO:10)

MVCFRLFPVPGSGLVLVCLVLGAVRSYALELNLTDSENATCLYAKWQMNFTVRYETT
NKTYKTVTISDHGTVTYNGSICGDDQNGPKIAVQFGPGFSWIANFTKAASTYSIDSV
SFSYNTGDNTTFPDAEDKGILTVDELLAIRIPLNDLFRCNSLSTLEKNDVVQHYWDV
LVQAFVQNGTVSTNEFLCDKDKTSTVAPTIHTTVPSPTTTPTPKEKPEAGTYSVNNG
NDTCLLATMGLQLNITQDKVASVININPNTTHSTGSCRSHTALLRLNSSTIKYLDFV
FAVKNENRFYLKEVNISMYLVNGSVFSIANNNLSYWDAPLGSSYMCNKEQTVSVSGA
FQINTFDLRVQPFNVTQGKYSTAQDCSADDDNFLVPIAVGAALAGVLILVLLAYFIG
LKHHHAGYEQF

Figure 3C

LAMP-2B coding sequence (human) (SEQ ID NO:2)

ATGGTGTGCTTCCGCCTCTTCCCGGTTCCGGGCTCAGGGCTCGTTCTGGTCTGCCTA
GTCCTGGGAGCTGTGCGGTCTTATGCATTGGAACTTAATTTGACAGATTCAGAAAAT
GCCACTTGCCTTTATGCAAAATGGCAGATGAATTTCACAGTTCGCTATGAAACTACA
AATAAAACTTATAAAACTGTAACCATTTCAGACCATGGCACTGTGACATATAATGGA
AGCATTTGTGGGGATGATCAGAATGGTCCCAAAATAGCAGTGCAGTTCGGACCTGGC
TTTTCCTGGATTGCGAATTTTACCAAGGCAGCATCTACTTATTCAATTGACAGCGTC
TCATTTTCCTACAACACTGGTGATAACACAACATTTCCTGATGCTGAAGATAAAGGA
ATTCTTACTGTTGATGAACTTTTGGCCATCAGAATTCCATTGAATGACCTTTTTAGA
TGCAATAGTTTATCAACTTTGGAAAAGAATGATGTTGTCCAACACTACTGGGATGTT
CTTGTACAAGCTTTTGTCCAAAATGGCACAGTGAGCACAAATGAGTTCCTGTGTGAT
AAAGACAAAACTTCAACAGTGGCACCCACCATACACACCACTGTGCCATCTCCTACT
ACAACACCTACTCCAAAGGAAAAACCAGAAGCTGGAACCTATTCAGTTAATAATGGC
AATGATACTTGTCTGCTGGCTACCATGGGGCTGCAGCTGAACATCACTCAGGATAAG
GTTGCTTCAGTTATTAACATCAACCCCAATACAACTCACTCCACAGGCAGCTGCCGT
TCTCACACTGCTCTACTTAGACTCAATAGCAGCACCATTAAGTATCTAGACTTTGTC
TTTGCTGTGAAAAATGAAAACCGATTTTATCTGAAGGAAGTGAACATCAGCATGTAT
TTGGTTAATGGCTCCGTTTTCAGCATTGCAAATAACAATCTCAGCTACTGGGATGCC
CCCCTGGGAAGTTCTTATATGTGCAACAAAGAGCAGACTGTTTCAGTGTCTGGAGCA
TTTCAGATAAATACCTTTGATCTAAGGGTTCAGCCTTTCAATGTGACACAAGGAAAG
TATTCTACAGCCCAAGAGTGTTCGCTGGATGATGACACCATTCTAATCCCAATTATA
GTTGGTGCTGGTCTTTCAGGCTTGATTATCGTTATAGTGATTGCTTACGTAATTGGC
AGAAGAAAAAGTTATGCTGGATATCAGACTCTGTAA

Figure 3D

LAMP-2B protein sequence (human) (SEQ ID NO:11)

MVCFRLFPVPGSGLVLVCLVLGAVRSYALELNLTDSENATCLYAKWQMNFTVRYETT
NKTYKTVTISDHGTVTYNGSICGDDQNGPKIAVQFGPGFSWIANFTKAASTYSIDSV
SFSYNTGDNTTFPDAEDKGILTVDELLAIRIPLNDLFRCNSLSTLEKNDVVQHYWDV
LVQAFVQNGTVSTNEFLCDKDKTSTVAPTIHTTVPSPTTTPTPKEKPEAGTYSVNNG
NDTCLLATMGLQLNITQDKVASVININPNTTHSTGSCRSHTALLRLNSSTIKYLDFV
FAVKNENRFYLKEVNISMYLVNGSVFSIANNNLSYWDAPLGSSYMCNKEQTVSVSGA
FQINTFDLRVQPFNVTQGKYSTAQECSLDDDTILIPIIVGAGLSGLIIVIVIAYVIG
RRKSYAGYQTL

Figure 3E

LAMP-2C coding sequence (human) (SEQ ID NO:3)

ATGGTGTGCTTCCGCCTCTTCCCGGTTCCGGGCTCAGGGCTCGTTCTGGTCTGCCTA
GTCCTGGGAGCTGTGCGGTCTTATGCATTGGAACTTAATTTGACAGATTCAGAAAAT
GCCACTTGCCTTTATGCAAAATGGCAGATGAATTTCACAGTTCGCTATGAAACTACA
AATAAAACTTATAAAACTGTAACCATTTCAGACCATGGCACTGTGACATATAATGGA
AGCATTTGTGGGGATGATCAGAATGGTCTCAAAATAGCAGTGCAGTTCGGACCTGGC
TTTTCCTGGATTGCGAATTTTACCAAGGCAGCATCTACTTATTCAATTGACAGCGTC
TCATTTTCCTACAACACTGGTGATAACACAACATTTCCTGATGCTGAAGATAAAGGA
ATTCTTACTGTTGATGAACTTTTGGCCATCAGAATTCCATTGAATGACCTTTTTAGA
TGCAATAGTTTATCAACTTTGGAAAAGAATGATGTTGTCCAACACTACTGGGATGTT
CTTGTACAAGCTTTTGTCCAAAATGGCACAGTGAGCACAAATGAGTTCCTGTGTGAT
AAAGACAAAACTTCAACAGTGGCACCCACCATACACACCACTGTGCCATCTCCTACT
ACAACACCTACTCCAAAGGAAAAACCAGAAGCTGGAACCTATTCAGTTAATAATGGC
AATGATACTTGTCTGCTGGCTACCATGGGGCTGCAGCTGAACATCACTCAGGATAAG
GTTGCTTCAGTTATTAACATCAACCCCAATACAACTCACTCCACAGGCAGCTGCCGT
TCTCACACTGCTCTACTTAGACTCAATAGCAGCACCATTAAGTATCTAGACTTTGTC
TTTGCTGTGAAAAATGAAAACCGATTTTATCTGAAGGAAGTGAACATCAGCATGTAT
TTGGTTAATGGCTCCGTTTTCAGCATTGCAAATAACAATCTCAGCTACTGGGATGCC
CCCCTGGGAAGTTCTTATATGTGCAACAAAGAGCAGACTGTTTCAGTGTCTGGAGCA
TTTCAGATAAATACCTTTGATCTAAGGGTTCAGCCTTTCAATGTGACACAAGGAAAG
TATTCTACAGCTGAAGAATGTTCTGCTGACTCTGACCTCAACTTTCTTATTCCTGTT
GCAGTGGGTGTGGCCTTGGGCTTCCTTATAATTGTTGTCTTTATCTCTTATATGATT
GGAAGAAGGAAAAGTCGTACTGGTTATCAGTCTGTGTAA

Figure 3F

LAMP-2C protein sequence (human) (SEQ ID NO:12)

MVCFRLFPVPGSGLVLVCLVLGAVRSYALELNLTDSENATCLYAKWQMNFTVRYETT
NKTYKTVTISDHGTVTYNGSICGDDQNGPKIAVQFGPGFSWIANFTKAASTYSIDSV
SFSYNTGDNTTFPDAEDKGILTVDELLAIRIPLNDLFRCNSLSTLEKNDVVQHYWDV
LVQAFVQNGTVSTNEFLCDKDKTSTVAPTIHTTVPSPTTTPTPKEKPEAGTYSVNNG
NDTCLLATMGLQLNITQDKVASVININPNTTHSTGSCRSHTALLRLNSSTIKYLDFV
FAVKNENRFYLKEVNISMYLVNGSVFSIANNNLSYWDAPLGSSYMCNKEQTVSVSGA
FQINTFDLRVQPFNVTQGKYSTAEECSADSDLNFLIPVAVGVALGFLIIVVFISYMI
GRRKSRTGYQSV

Figure 4A. LAMP-2A

```
Human      (SEQ ID NO:4)  WDAPLGSSYMCNKEQTVSVSGAFQINTFDLRVQPFNVTQGKYSTAQDCSADDDNFLVPIAVGAALAGVLILVLL
Identities                WDAPLGSSYMCNKEQ   SVS AFQINTF L VQPFNVT G YSTAQDCSAD DNFLVPIAVGAAL GVLILVLL
Mouse      (SEQ ID NO:5)  WDAPLGSSYMCNKEQVLSVSRAFQINTFNLKVQPFNVTKGQYSTAQDCSADEDNFLVPIAVGAALGGVLILVLL Human              AYFIGLKHHHAGYEQF
Identities         AYFIGLK HH GYEQF
Mouse              AYFIGLKRHHTGYEQF
```

Figure 4B. LAMP-2B

```
Human      (SEQ ID NO:6)  WDAPLGSSYMCNKEQTVSVSGAFQINTFDLRVQPFNVTQGKYSTAQECSLDDTILIPIIVGAGLSGLIIVIVIAY
Identities                WDAPLGSSYMCNKEQ   SVS AFQINTF L VQPFNVT G YSTAQECSLDDTILIPIIVGAGLSGLIIVIVIAY
Mouse      (SEQ ID NO:7)  WDAPLGSSYMCNKEQVLSVSRAFQINTFNLKVQPFNVTKGQYSTAQECSLDDTILIPIIVGAGLSGLIIVIVIAY Human              VIGRRKSYAGYQTL
Identities         IGRRK YAGYQTL
Mouse              LIGRRKTYAGYQTL
```

Figure 4C. LAMP-2C

```
Human      (SEQ ID NO:8)  WDAPLGSSYMCNKEQTVSVSGAFQINTFDLRVQPFNVTQGKYSTAEECSADSDLNFLIPVAVGVALGFLIIVFISYMIG
Identities                WDAPLGSSYMCNKEQ   SVS AFQINTF L VQPFNVT G YSTAEEC ADSDLNFLIPVAVGVALGFLII VFISYMIG
Mouse      (SEQ ID NO:9)  WDAPLGSSYMCNKEQVLSVSRAFQINTFNLKVQPFNVTKGQYSTAEECAADSDLNFLIPVAVGVALGFLIIAVFISYMIG Human              RRKSRTGYQSV
Identities         RRKSRTGYQSV
Mouse              RRKSRTGYQSV
```

WT Control

AAV9.EGFP ($2\times10^{12}$ gc)

AAV9.LAMP-2B ($2\times10^{12}$ gc)

AAV9.EGFP ($5 \times 10^{11}$ gc)

AAV9.LAMP-2B ($5 \times 10^{11}$ gc)

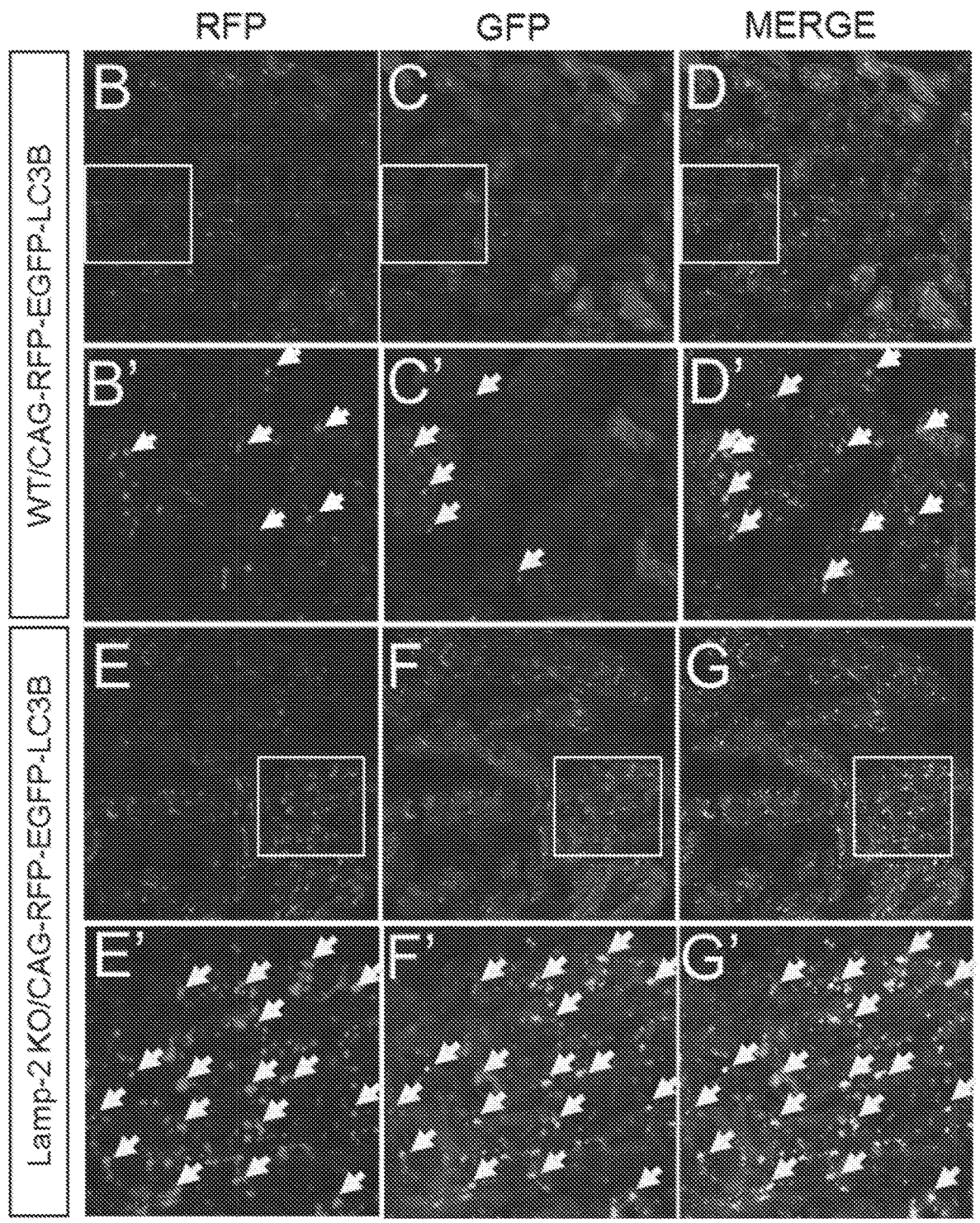
FIG. 9B-G'

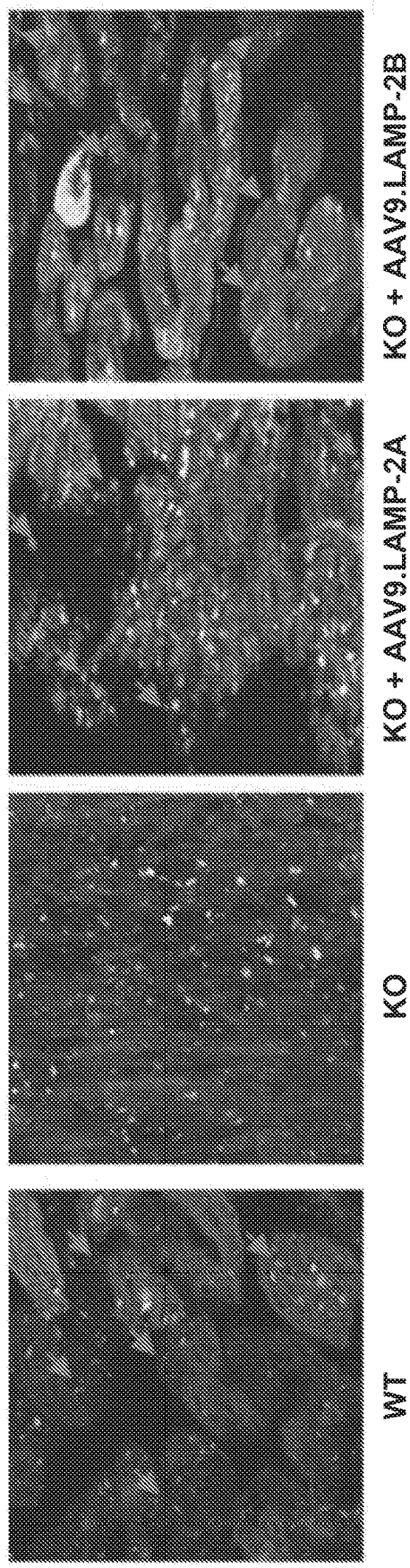

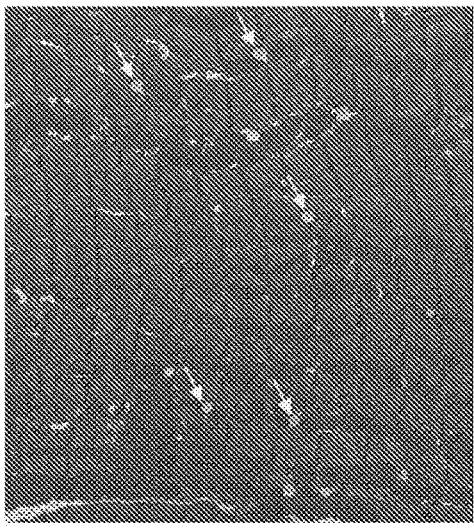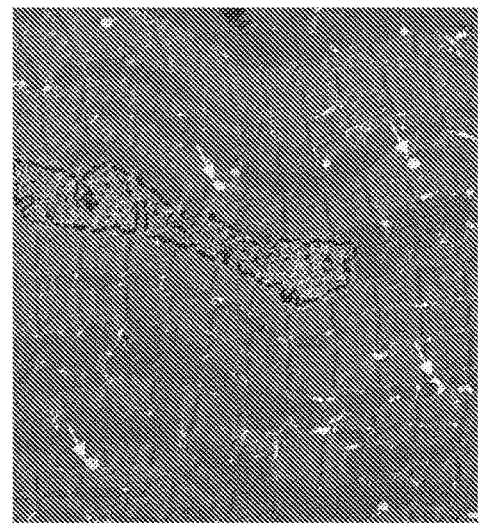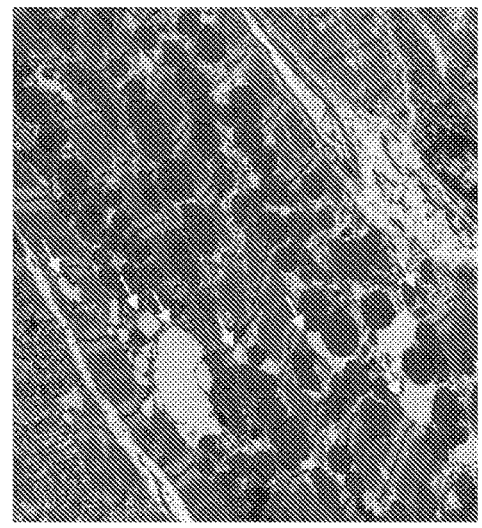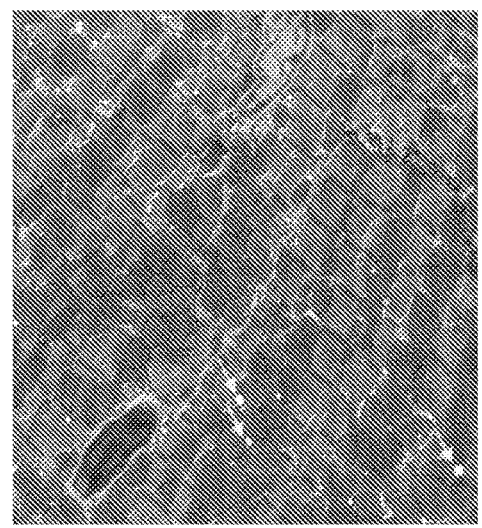

METHODS FOR THE TREATMENT OF DANON DISEASE AND OTHER DISORDERS OF AUTOPHAGY

This patent application is a U.S. National Phase application of International Patent Application PCT/US2017/014164 filed Jan. 19, 2017, which claims priority pursuant to 35 U.S.C. § 119(e) to U.S. Provisional Patent Application Ser. No. 62/280,269, filed Jan. 19, 2016, both of which are hereby incorporated by reference in its entirety.

This invention was made with government support under HL107755 awarded by the National Institutes of Health. The government has certain rights in this invention.

BACKGROUND

Danon disease is a familial cardiomyopathy associated with impaired autophagy due to mutations in the gene encoding lysosome-associated membrane protein 2 (LAMP-2, also known as CD107b). Emerging evidence has highlighted the importance of autophagy in regulating cardiomyocyte bioenergetics, function, and survival. However, the mechanisms responsible for cellular dysfunction and death in cardiomyocytes with impaired autophagic flux remain unclear. In a previous study, to investigate the molecular mechanisms responsible for Danon disease, we created human induced pluripotent stem cells (hiPSCs) from two patients with different LAMP-2 mutations (Hashem, et al., *Stem Cells.* 2015 July; 33(7):2343-50). Danon hiPSC-derived cardiomyocytes (hiPSC-CMs) exhibited impaired autophagic flux and key features of heart failure such as increased cell size, increased expression of natriuretic peptides, and abnormal calcium handling compared to control hiPSC-CMs. Additionally, Danon hiPSC-CMs demonstrated excessive amounts of mitochondrial oxidative stress and apoptosis. Using the sulfhydryl antioxidant N-acetylcysteine to scavenge free radicals resulted in a significant reduction in apoptotic cell death in Danon hiPSC-CMs. We also used a lentiviral vector to introduce the coding sequence of the LAMP-2B isoform under the control of a doxycycline-inducible promoter in one of the Danon hiPSC lines. Overexpression of LAMP-2B with the addition of doxycycline also reduced oxidative stress levels and apoptotic cell death in Danon hiPSC-CMs, confirming the importance of LAMP-2B in disease pathophysiology. In summary, we modeled Danon disease using hiPSC-CMs from patients with mutations in LAMP-2, allowing us to gain mechanistic insight into the pathogenesis of this disease. We demonstrated that LAMP-2 deficiency led to an impairment in autophagic flux, which resulted in excessive oxidative stress, and subsequent cardiomyocyte apoptosis. Scavenging excessive free radicals with antioxidants and overexpression of LAMP-2B improved the disease phenotype in vitro. The prior art does not disclose effective treatment strategies for Danon disease or other diseases associated with autophagy, thus the in vivo studies presented herein were necessary to validate the approach.

SUMMARY

In one aspect, provided are gene therapy vectors, e.g., for use in systemically or locally increasing the expression of one or more isoforms of lysosome-associated membrane protein 2 (LAMP-2) in a subject. The gene therapy vectors find use in preventing, mitigating, ameliorating, reducing, inhibiting, and/or treating one or more symptoms of Danon disease or another disorder of insufficient autophagic flux. In varying embodiments, the gene therapy vectors comprise an expression cassette comprising a polynucleotide encoding one or more isoforms of lysosome-associated membrane protein 2 (LAMP-2). In varying embodiments, the vector is a viral vector. In varying embodiments, the viral vector is from a virus selected from the group consisting of adenovirus, retrovirus, lentivirus, herpesvirus and adeno-associated virus (AAV). In varying embodiments, the vector is from one or more of adeno-associated virus (AAV) serotypes 1-11, or any subgroups thereof. In varying embodiments, the viral vector is encapsulated in an anionic liposome. In varying embodiments, the vector is a non-viral vector. In varying embodiments, the non-viral vector is selected from the group consisting of naked DNA, a cationic liposome complex, a cationic polymer complex, a cationic liposome-polymer complex, and an exosome. In varying embodiments, the expression cassette comprises operably linked in the 5' to 3' direction (from the perspective of the mRNA to be transcribed), a first inverse terminal repeat, an enhancer, a promoter, the polynucleotide encoding one or more isoforms of LAMP-2, a 3' untranslated region, polyadenylation (polyA) signal, and a second inverse terminal repeat. In varying embodiments, the promoter is selected from the group consisting of cytomegalovirus (CMV) promoter and chicken-beta actin (CAG) promoter. In varying embodiments, the polynucleotide comprises DNA or cDNA. In varying embodiments, the polynucleotide encoding one or more isoforms of LAMP-2 comprises one or more human LAMP-2 isoforms. In varying embodiments, the polynucleotide encoding one or more isoforms of LAMP-2 comprises one or more LAMP-2 isoforms selected from the group consisting of LAMP-2A, LAMP-2B, and LAMP-2C. In varying embodiments, the polynucleotide encoding one or more isoforms of LAMP-2 has at least about 90% sequence identity, e.g., at least about 91%, 92%, 93%, 94%, 95%, 96%, 97%, 98%, 99% sequence identity, to one or more of SEQ ID NO:1, SEQ ID NO:2 and SEQ ID NO:3. In varying embodiments, the polynucleotide encoding one or more isoforms of LAMP-2 comprises one or more of SEQ ID NO:1, SEQ ID NO:2 and SEQ ID NO:3.

In a further aspect, provided are methods of preventing, mitigating, ameliorating, reducing, inhibiting, eliminating and/or reversing one or more symptoms of Danon disease or another autophagy disorder in a subject in need thereof, comprising administering to the subject a gene therapy vector as described above and herein (see for example FIG. 2). In a further aspect, provided are methods of preventing, mitigating, ameliorating, reducing, inhibiting, eliminating and/or reversing one or more symptoms of Danon disease or another autophagy disorder in a subject in need thereof, comprising administering to the subject an adeno-associated virus (AAV) vector comprising an expression cassette comprising a polynucleotide encoding one or more isoforms of lysosome-associated membrane protein 2 (LAMP-2). In varying embodiments, the vector is administered via a route selected from the group consisting of intravenous, intraarterial, intracardiac, intracoronary, intramyocardial, intrarenal, intraurethral, epidural, intracranial, subcutaneous, and intramuscular. In varying embodiments, the vector is delivered or administered via a physical or mechanical method selected from the group consisting of microinjection, jet injection, particle bombardment, hydrodynamic infusion, electroporation, sonoporation, laser irradiation, magnetofection. In varying embodiments, the vector is administered multiple times with or without immunosuppression or plasmapheresis of the patient. In varying embodiments, the autophagy disorder is selected from the group consisting of end-stage heart failure, myocardial infarction, drug toxicities, diabetes, end-stage renal failure, and aging. In varying embodiments, the subject is human. In varying embodiments, the subject is exhibiting symptoms of Danon disease or another autophagy disorder. In varying embodiments, the subject has been identified as having reduced or non-detectable LAMP-2 expression. In varying embodiments, the subject has been identified as having a mutated LAMP-2 gene.

Definitions

The term "Danon disease" refers to an X-linked dominant skeletal and cardiac muscle disorder with multisystem clinical manifestations. Danon disease mutations lead to an absence of lysosome-associated membrane protein 2 (LAMP-2) protein expression. Major clinical features include skeletal and cardiac myopathy, cardiac conduction abnormalities, cognitive difficulties, and retinal disease. Men are typically affected earlier and more severely than women.

The terms "lysosome-associated membrane protein 2" and "LAMP-2" interchangeably refer to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 300, 400, or more amino acids, or over the full-length, to an amino acid sequence encoded by a LAMP-2 nucleic acid (see, e.g., GenBank Accession Nos. NM_002294.2 (isoform A). NM_013995.2 (isoform B), NM_0011222606.1 (isoform C)) or to an amino acid sequence of a LAMP-2 polypeptide (see e.g. GenBank Accession Nos. NP_002285.1 (isoform A), NP_054701.1 (isoform B), NP_001116078.1 (isoform C)); (2) bind to antibodies, e.g., polyclonal antibodies, raised against an immunogen comprising an amino acid sequence of a LAMP-2 polypeptide (e.g., LAMP-2 polypeptides described herein); or an amino acid sequence encoded by a LAMP-2 nucleic acid (e.g., LAMP-2 polynucleotides described herein), and conservatively modified variants thereof; (3) specifically hybridize under stringent hybridization conditions to an anti-sense strand corresponding to a nucleic acid sequence encoding a LAMP-2 protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a LAMP-2 nucleic acid (e.g., LAMP-2 polynucleotides, as described herein, and LAMP-2 polynucleotides that encode LAMP-2 polypeptides, as described herein).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W); and
7) Serine (S), Threonine (T)

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., LAMP-2 polynucleotide or polypeptide sequence as described herein, when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, for example, over a region that is 50, 100, 200, 300, 400 amino acids or nucleotides in length, or over the full-length of a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to LAMP-2 nucleic acids and proteins, the BLAST and BLAST 2.0 algorithms and the default parameters are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds., Current Protocols in Molecular Biology (1995 supplement)). Examples of algorithms that are suitable for determining percent sequence identity and sequence similarity are the BLAST and BLAST 2.0 algorithms, which are described in Altschul et al., J. Mol. Biol. 215:403-410 (1990) and Altschul et al., Nucleic Acids Res. 25:3389-3402 (1977), respectively. Software for performing BLAST analyses is publicly available through the National Center for Biotechnology Information (on the worldwide web at ncbi.nlm.nih.gov/).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

As used herein, "administering" refers to local and systemic administration, e.g., including enteral, parenteral, pulmonary, and topical/transdermal administration. Routes of administration for compounds (e.g., polynucleotide encoding one or more LAMP-2 isoforms) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intraarterial, intrarenal, intraurethral, intracardiac, intracoronary, intramyocardial, intradermal, epidural, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administering" or "concurrent administration", when used, for example with respect to the compounds (e.g., LAMP-2 polynucleotides) and/or analogs thereof and another active agent, refers to administration of the compound and/or analogs and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, e.g., 30% or 40% or greater, e.g., 50% or 60% or greater, e.g., 70% or 80% or 90% or greater) of their maximum serum concentration for any given dose.

The term "effective amount" or "pharmaceutically effective amount" refer to the amount and/or dosage, and/or dosage regime of one or more compounds (e.g., gene therapy vectors) necessary to bring about the desired result e.g., increased expression of one or more LAMP-2 isoforms in an amount sufficient to reduce the ultimate severity of a disease characterized by impaired or deficient autophagy (e.g., Danon disease).

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The phrase "in conjunction with" when used in reference to the use of the active agent(s) described herein (e.g., one or more isoforms of a LAMP-2 polynucleotide) in conjunction with one or more other drugs described herein (e.g., an acetylcholinesterase inhibitor) the active agent(s) and the other drug(s) are administered so that there is at least some chronological overlap in their physiological activity on the organism. When they are not administered in conjunction with each other, there is no chronological overlap in physiological activity on the organism. In certain preferred embodiments, the "other drug(s)" are not administered at all (e.g., not co-administered) to the organism.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, e.g., measurable and sustained increase in the expression levels of one or more isoforms of LAMP-2.

As used herein, the phrase "consisting essentially of" refers to the genera or species of active pharmaceutical agents recited in a method or composition, and further can include other agents that, on their own do not have substantial activity for the recited indication or purpose.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments, the subject may not be under the care or prescription of a physician or other healthworker.

The terms "gene transfer" or "gene delivery" refer to methods or systems for reliably inserting foreign DNA into host cells. Such methods can result in transient expression of non-integrated transferred DNA, extrachromosomal replication and expression of transferred replicons (e.g. episomes), or integration of transferred genetic material into the genomic DNA of host cells.

By an "AAV vector" is meant a vector derived from an adeno-associated virus serotype, including without limitation, AAV1, AAV2, AAV3, AAV4, AAV5, AAV6, etc. AAV vectors can have one or more of the AAV wild-type genes deleted in whole or part, e.g., the rep and/or cap genes, but retain functional flanking inverted terminal repeat (ITR) sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g. by the insertion, deletion or substitution of nucleotides, as long as the sequences provide for functional rescue, replication and packaging. AAV expression vectors are constructed using known techniques to at least provide as operatively linked components in the direction of transcription, control elements including a transcriptional initiation region, the DNA of interest (i.e. the LAMP-2 gene) and a transcriptional termination region.

BRIEF DESCRIPTION OF THE DRAWINGS

FIG. 1 illustrates schematics of Adeno-Associated Virus LAMP-2 Gene Delivery Constructs. The indicated lysosome-associated membrane protein (LAMP) LAMP-2 coding region generally should be understood to include the upstream ribosome binding sequence and start codon, but in some embodiments the native element can be substituted with a heterologous one. The upstream ribosome binding site is not used in combinations with coding regions downstream of an IRES or self-cleaving peptide. The start codon is not necessarily present in coding regions downstream of a self-cleaving peptide. FIGS. 1A-1F show vector genomes containing one LAMP-2 isoform. FIGS. 1G-1K show vector genomes containing two LAMP-2 isoforms. FIGS. 1L-1O show vector genomes containing all three LAMP-2 isoforms. The following abbreviations are used in the figure: ITR: Inverse terminal repeat; LAMP-2: Lysosomal associated membrane protein type 2; UTR: Untranslated region; Poly A: Polyadenylation signal; CAG: Promoter region comprising CMV enhancer and CBA promoter sequences; CMV: Cytomegalovirus; CBA: Chicken beta-actin; WPRE: Woodchuck hepatitis virus posttranscriptional regulatory element; RBG: Rabbit beta-globin polyadenylation signal; EF-1: Human elongation factor-1; IRES: Internal ribosome entry site; P2A: 2A peptide.

FIG. 1A shows a schematic of a construct containing protein coding information for one LAMP-2 isoform—A, B, or C—with generic 5' and 3' control regions.

FIG. 1B shows a schematic of the construct of some embodiments and used in the Examples below consisting of the 5' and 3' inverse terminal repeat elements, a CAG promoter region containing the CMV enhancer and CBA promoter sequences, the CBA intron, the coding sequence for one of the LAMP-2 isoforms including the upstream ribosomal binding sequence and start codon, the WPRE sequence as the 3' UTR, and the rabbit beta-globin polyadenylation signal.

FIG. 1C shows a schematic of a construct containing the native human LAMP-2 promoter region. In some embodiments, this construct is used to express the transgene in response to cellular signals that would typically result in LAMP-2 expression in normal cells.

FIG. 1D shows a schematic of a construct containing the human elongation factor-1 alpha promoter. In some embodiments, this construct is used to express the transgene constitutively under the control of a human promoter region. Other constitutively active human promoters could also be used in place of EF-1 alpha.

FIG. 1E shows a schematic of a construct containing a cardiac-specific promoter such as, but not limited to, the cardiac troponin T2 promoter. In some embodiments, this construct is used to express the transgene only in cardiac tissue (and, for example, avoid hepatic expression).

FIG. 1F shows a schematic of a construct containing a muscle-specific promoter such as, but not limited to, the creatinine muscle kinase promoter. In some embodiments, this construct is used to express the transgene in cardiac and skeletal muscle (and avoid extra-muscular expression).

FIG. 1G shows a schematic of a construct containing the coding sequences for two LAMP-2 isoforms (using any potential combination) under the control of different promoter regions. In some embodiments, this construct (and those of FIGS. 1H to 1K) is used to express two different LAMP-2 isoforms using the same viral genome.

FIG. 1H shows a schematic of a construct containing the sequences for two LAMP-2 isoforms (using any potential combination) under the control of different promoter regions. One isoform is coded in the (+) direction on the single-stranded AAV genome and the other isoform is coded in the (−) direction. In some embodiments, this construct is used to express two different LAMP-2 isoforms on separate DNA strands.

FIG. 1I shows a schematic of a construct containing the coding sequences for two LAMP-2 isoforms (using any potential combination) under the control of a promoter region and an internal ribosome entry site, respectively, and followed by 3' UTR and Poly A signals. In some embodiments, this construct is used to express two different LAMP-2 isoforms using the same viral genome.

FIG. 1J shows a schematic of a construct containing the coding sequences for two LAMP-2 isoforms (using any potential combination) separated by a P2A cleavage site. In some embodiments, this construct is used to express an mRNA encoding two different LAMP-2 isoforms in a single polypeptide, which would spontaneously cleave into the individual LAMP-2 protein isoforms following translation via the 2A peptide self-cleavage, using the same viral genome.

FIG. 1K shows a schematic of a construct containing the coding sequence for LAMP-2 exons 1-8 followed by an intronic region (containing all necessary splice signals), the exon 9 coding sequence for one of the LAMP-2 isoforms with the 3' UTR and Poly A signal, a second intronic region (containing all necessary splice signals), and the exon 9 coding sequence for a different LAMP-2 isoform (in any potential combination) with the 3' UTR and Poly A signal. In some embodiments, this construct is used to express mRNAs for two different LAMP-2 isoforms via alternative splicing, which is the mechanism that generates the different LAMP-2 mRNAs in normal cells, using the same viral genome.

FIG. 1L shows a schematic of a construct containing the coding sequences for all three LAMP-2 isoforms, with 3' UTR and Poly A signals, under the control of different promoter regions. In some embodiments, this construct is used to express all three of the different LAMP-2 isoforms using the same viral genome and would allow for restoration of all potential LAMP-2 functions.

FIG. 1M shows a schematic of a construct containing the coding sequences for all three LAMP-2 isoforms, in any order, under the control of a promoter region and two different internal ribosome entry sites, followed by 3' UTR and Poly A signals. In some embodiments, this construct is used to express all three LAMP-2 isoforms using the same viral genome.

FIG. 1N shows a schematic of a construct containing the coding sequences for all three LAMP-2 isoforms, in any potential order, separated by a P2A cleavage sites. In some embodiments, this construct is used to express an mRNA encoding the three different LAMP-2 isoforms in a single polypeptide, which would spontaneously cleave into the individual LAMP-2 protein isoforms following translation via 2A peptide self-cleavage, using the same viral genome.

FIG. 1O shows a schematic of a construct containing the coding sequence for LAMP-2 exons 1-8 followed by an intronic region (containing all necessary splice signals), the exon 9 coding sequence for one of the LAMP-2 isoforms with the 3' UTR and Poly A signal, a second intronic region (containing all necessary splice signals), and the exon 9 coding sequence for a second LAMP-2 isoform with the 3' UTR and Poly A signal, a third intronic region (containing all necessary splice signals), and the exon 9 coding sequence for a third LAMP-2 isoform with 3' UTR and Poly A signal. In some embodiments, this construct is used to express mRNAs for all three LAMP-2 isoforms via alternative splicing, which is the mechanism that generates the different LAMP-2 mRNAs in normal cells, using the same viral genome. The exon 9 coding sequences could be placed in any potential order and combination.

FIG. 3A-F depict LAMP-2 isoform coding and protein sequences: FIG. 3A: LAMP-2A coding sequence; FIG. 3B: LAMP-2A protein sequence; FIG. 3C: LAMP-2B coding sequence; FIG. 3D: LAMP-2B protein sequence; FIG. 3E: LAMP-2C coding sequence; and FIG. 3F: LAMP-2C protein sequence.

FIG. 4A-C presents a comparison of the last 90 amino acids of the human and mouse protein sequences of LAMP-2A (FIG. 4A), LAMP-2B (FIG. 4B), and LAMP-2C (FIG. 4C) showing sequence identities.

FIG. 7A shows a heart section from a Lamp-2 knock out (KO) mouse treated with AAV9.LAMP-2B. FIG. 7B shows a heart section from a Lamp-2 KO mouse treated with AAV9.EGFP. FIG. 7C shows a heart section from an untreated wild type (WT) mouse.

FIG. 7A shows a heart section from a Lamp-2 KO mouse treated with AAV9.LAMP-2B. FIG. 7B shows a heart section from a Lamp-2 KO mouse treated with AAV9.EGFP.

FIG. 9A-H illustrates the CAG-RFP-EGFP-LC3B autophagy reporter system. FIG. 9A presents a schematic representation of the operation of the system. FIG. 9B-G' are fluorescence microscopy images; the X' (X prime) images being enlargements of the insets outlined on the images labeled with the same letter without the prime. With respect to the FIG. 9B-G' grid; the first column are images of red fluorescence; the second column are images of green fluorescence; the third column are merged images of the first and second columns, yellow representing red+green fluorescence; the top two rows are images of heart sections from WT mice expressing the CAG-RFP-EGFP-LC3B autophagy reporter construct; the bottom two rows are images of heart sections from Lamp-2 KO mice expressing the CAG-RFP-EGFP-LC3B autophagy reporter construct. Immature autophagosomes fluoresce both green and red (or yellow in the merged images). Mature autolysosomes fluoresce only red. Yellow arrows highlight autophagic vacuoles fluorescing in both colors while white arrows highlight autophagic vacuoles fluorescing only in red. FIG. 9H illustrates the number of autophagic vacuoles that are autophagosomes or autolysosomes in WT and Lamp-2 KO mice.

FIG. 10A-E illustrates the effect of -2 gene therapy using the CAG-RFP-EGFP-LC3B autophagy reporter system. FIG. 10A is an image of untreated WT mouse heart section. FIG. 10B is an image of a heart section showing transduced cells from a Lamp-2 KO mouse treated with the control vector AAV9.EGFP. FIG. 10C is an image of a heart section from a Lamp-2 KO mouse treated with the gene therapy vector AAV9.LAMP-2A. FIG. 10D is an image of a heart section from a Lamp-2 KO mouse treated with the gene therapy vector AAV9.LAMP-2B. In the images of FIGS. 10A, 10C and 10D red arrows are used to highlight some of the autolysosomes present. FIG. 10E illustrates the proportion of total autophagic vacuoles represented by autophagosomes and autolysosomes for the four conditions.

FIG. 11A-C' presents electron micrographs of heart tissue from WT (FIG. 11A, A') and Lamp-2 KO (FIG. 11B, B') mice, and a Lamp-2 KO mouse treated with AAV9.LAMP-2B (FIG. 11C, C'). White arrows highlight some of the autophagic vacuoles. Black arrows highlight some of the damaged mitochondria.

DETAILED DESCRIPTION

1. Introduction

Figure 2:
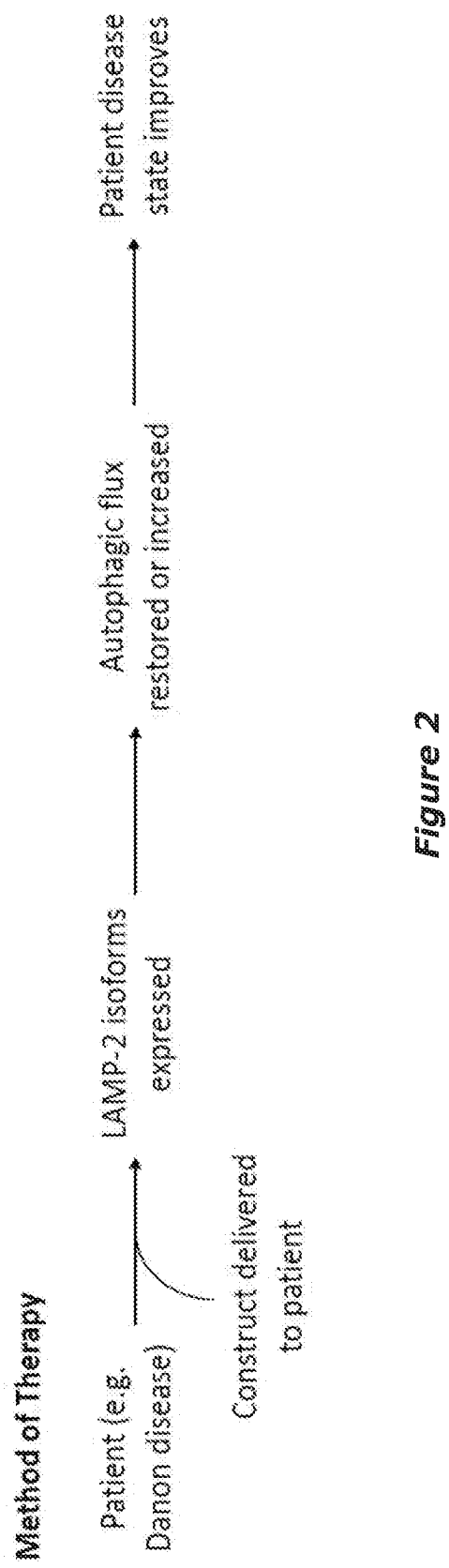
FIG. 2 illustrates a flow chart of a method of therapeutic treatment (e.g., of Danon disease or another disease caused at least in part by an autophagy deficiency) by promoting the expression of one or more isoforms of LAMP-2.

Danon disease is caused by mutations resulting in reduced or absent expression of the lysosome-associated membrane protein 2 (LAMP-2, also known as CD107b) gene. The present methods are based in part, on the introduction of one or more polynucleotides encoding one or more LAMP-2 isoforms, e.g., packaged in an adeno-associated virus (AAV) vector, to deliver the LAMP-2 gene/individual isoforms to Danon patients. After delivery of the one or more polynucleotides encoding one or more LAMP-2 isoforms, the LAMP-2 transgene is then expressed by the patient's own cells. Restoration of LAMP-2 gene expression in Danon patients can result in amelioration of the disease phenotype, serving as a therapy for this disease. Delivery to a subject of one or more polynucleotides encoding one or more LAMP-2 isoforms also can be used for the treatment of other disorders of autophagy including, but not limited to, end-stage heart failure, myocardial infarction drug toxicities, diabetes, end-stage renal failure, and aging. Abnormalities in autophagy, particularly decreased autophagic flux, have been implicated in these disorders as well as many others. Expressing higher levels of the LAMP-2 gene increases autophagic flux and therefore serves as a treatment for these disorders.

No current art exists for treating Danon disease by gene therapy methods. Danon disease is not a traditional lysosomal storage disorder, which is generally defined as a deficiency in a lysosomal protein (e.g. a transporter or enzyme) that is required for processing a specific cellular substrate, which results in a toxic accumulation of that specific substrate within lysosomes. Danon disease is understood to be a disorder of autophagy or an autophagic vacuolar myopathy, which affects the degradation of all cellular components processed by the autophagic pathway and is not caused by the accumulation of specific substrate. Additionally, no existing art explicitly describes the delivery of the LAMP-2 gene/individual isoforms for treatment of Danon disease or other disorders of autophagy. Therefore, the present methods provide a unique method for treating Danon disease and improves upon existing AAV technologies by explicitly including delivery of the LAMP-2 gene as a means for improving disorders of autophagy.

2. Patients Subject to Treatment

Subjects/patients amenable to treatment using the methods described herein include individuals at risk of a disease or disorder characterized by insufficient autophagic flux (e.g., Danon disease as well as other known disorders of autophagy including, but not limited to, systolic and diastolic heart failure, myocardial infarction, drug toxicities (for example, anthracyclines chloroquine and its derivatives), diabetes, end-stage renal disease, and aging) but not showing symptoms, as well as subjects presently showing symptoms. Such subject may have been identified as having a mutated LAMP-2 gene or as having reduced or non-detectable levels of LAMP-2 expression.

In some embodiments, the subject is exhibiting symptoms of a disease or disorder characterized by insufficient autophagic flux (e.g., Danon disease as well as other known disorders of autophagy including, but not limited to, systolic and diastolic heart failure, myocardial infarction, drug toxicities, diabetes, end-stage renal disease, and aging). The symptoms may be actively manifesting, or may be suppressed or controlled (e.g., by medication) or in remission. The subject may or may not have been diagnosed with the disorder, e.g., by a qualified physician.

The subject can be any mammal at any stage of development at the time of delivery, e.g., embryonic, fetal, infantile, juvenile or adult. In varying embodiments, the subject is a child, a juvenile or an adult. In varying embodiments, the subject is a mammal, for example, a human or a domesticated mammal (e.g., a canine or a feline).

3. Delivery Vectors of LAMP-2 Polynucleotide

Generally, the gene therapy vectors described herein comprise an expression cassette comprising a polynucleotide encoding one or more isoforms of lysosome-associated membrane protein 2 (LAMP-2), that allows for the expression of LAMP-2 to partially or wholly rectify deficient LAMP-2 protein expression levels and autophagic flux in a subject in need thereof (e.g., a subject having Danon disease or another disorder characterized by deficient autophagic flux at least in part due to deficient LAMP-2 expression). The gene therapy vectors can be viral or non-viral vectors. Illustrative non-viral vectors include, e.g., naked DNA, cationic liposome complexes, cationic polymer complexes, cationic liposome-polymer complexes, and exosomes.

In some embodiments the vector carries a single isoform, LAMP-2A, LAMP-2B, or LAMP-2C; see for example FIG. 1A-F showing a schematic of an AAV vector carrying a gene for a single LAMP-2 isoform. In other embodiments the vector carries genes for two LAMP-2 isoforms; see for example FIG. 1G-K showing a schematic of AAV vectors carrying a gene for a two LAMP-2 isoforms, LAMP-2B on one DNA strand and LAMP-2A on the other DNA strand. Still other embodiments carry all three isoforms (See FIG. 1L-O). In addition to the depicted genome structures three isoform vectors could also be constructed by making hybrids of the various embodiments shown. For example, there could be two promoters, one driving expression of a single isoform and the other driving expression of a two isoform cassette making use of an IRES, a self-cleaving peptide, or alternative splicing. In various embodiments comprising multiple isoforms, the isoforms occur in any order, either mirroring the natural order of B, A, C, or altering it. By carrying multiple isoforms in a single vector one can ensure co-expression of the isoforms in the transfected cells and use fewer total vector particles in a dose.

Examples of viral vector include, but are not limited, to adenoviral, retroviral, lentiviral, herpesvirus and adeno-associated virus (AAV) vectors. Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction, Such recombinant viruses may be produced by techniques known in the art, e.g., by transfecting packaging cells or by transient transfection with helper plasmids or viruses. Typical examples of virus packaging cells include but are not limited to PA317 cells, PsiCRIP cells, GPenv+ cells, 293 cells, etc. Detailed protocols for producing such replication-defective recombinant viruses may be found for instance in WO95/14785, WO96/22378, U.S. Pat. Nos. 5,882,877, 6,013,516, 4,861,719, 5,278,056 and WO94/19478, the complete contents of each of which is hereby incorporated by reference.

In some embodiments, the gene viral vector is an adenoviral vector or an adeno-associated viral (AAV) vector. In varying embodiments, the AAV vector is selected from AAV serotypes AAV1, AAV2, AAV3, AAV4, AA5, AAV6, AAV7, AAV8, AAV9, AAV10, AAV11, AAVrh10, and subgroups and mixtures thereof including self-complementary AAV (scAAV) genomes, or any other serotypes of AAV that can infect humans, monkeys or other species. In one embodiment, the AAV vector is an AAVrh10. In another embodiment the AAV vector is AAV9. In still another embodiment the AAV vector is AAV8. Recombinant AAV (rAAV) vectors are frequently utilized for the delivery of therapeutic genes and have been studied in human clinical trials. rAAV vectors can be designed to deliver specified transgenes to a patient's cells for expression. After infection and introduction of the viral genome by the rAAV vector, the viral genes exist mostly as extrachromosomal structures that do not integrate into the host's genome, but are expressed by the host cell's translational machinery. For successful host cell infection and gene expression, rAAV vectors require several components (see FIG. 1): inverse terminal repeat elements (ITRs), promoter and/or enhancer region, transgene, and 3' untranslated region, and polyadenylation signal. After viral infection of host cells, the promoter region initiates signals for translation of the virally delivered transgene by the host cell's translational machinery.

Generally, the control elements are selected to be functional in a mammalian cell. The resulting construct which contains the operatively linked components is bounded (5' and 3) with functional AAV ITR sequences. By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. See, e.g., Kotin, 1994; Berns, K I "Parvoviridae and their Replication" in Fundamental Virology, 2nd Edition, (B. N. Fields and D. M. Knipe, eds., the complete contents of which is hereby incorporated by reference) for the AAV2 sequence. As used herein, an "AAV ITR" does not necessarily comprise the wild-type nucleotide sequence, but may be altered, e.g., by the insertion, deletion or substitution of nucleotides.

Additionally, the AAV ITR may be derived from any of several AAV serotypes, including without limitation, AAV1, AAV2, AAV3, AAV4, AA5, AAV6, AAV7, AAV8, AAV9, AAV10, AAV11, AAVrh10. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Additionally, AAV ITRs may be derived from any of several AAV serotypes, including without limitation, AAV1, AAV2, AAV3, AAV4, AA5, AAV6, AAV7, AAV8, AAV9, AAV10, AAV11, AAVrh10. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In varying embodiments, vectors derived from AAV serotypes having tropism for, and high transduction efficiencies in, cells of the mammalian myocardium are employed, particularly cardiomyocytes and cardiomyocyte progenitors. A review and comparison of transduction efficiencies of different serotypes is provided in Cearley C N et al., Molecular Therapy 16(10); 1710-1718, 2008, the complete contents of which is hereby incorporated by reference. In other non-limiting examples, preferred vectors include vectors derived from any serotypes like AAV1, AAV2, AAV3, AAV4, AA5, AAV6, AAV7, AAV8, AAV9, AAV10, AAV11 or AAVrh10, which have also been shown to transduce cells of cardiomyocytes.

In varying embodiments, the selected nucleotide sequence is operably linked to control elements that direct the transcription or expression thereof in the subject in vivo. Such control elements can comprise control sequences normally associated with the selected gene.

Alternatively, heterologous control sequences can be employed. Useful heterologous control sequences generally include those derived from sequences encoding mammalian or viral genes. Examples include, but are not limited to, the phophoglycerate kinase (PKG) promoter, CAG (CMV enhancer with chicken beta-actin promoter including sequence through the 1st intron and the splice acceptor of the rabbit beta-globin gene) promoter, MCK (muscle creatine kinase) promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), rous sarcoma virus (RSV) promoter, synthetic promoters, hybrid promoters, and the like. The promoters can be of human origin or from other species, including from mice. In addition, sequences derived from non-viral genes, such as the marine metallothionein gene, will also find use herein. Such promoter sequences are commercially available from, e.g. Stratagene (San Diego, Calif.). Examples of heterologous promoters include but are not limited to the CMV promoter. Examples of inducible promoters include but are not limited to DNA responsive elements for ecdysone, tetracycline, and hypoxia andaufin. When multiple isoforms are encoded in a single vector they are preferably, but not necessarily, operably linked to different control sequences.

Similarly, control elements at the 3' end of a coding region, including a 3' untranslated region (3' UTR) and a polyadenylation signal, can derive from the inserted gene or from a heterologous source. Particular embodiments utilize the woodchuck hepatitis virus posttranscriptional regulatory element (WPRE) as a 3' UTR or a rabbit beta-globin polyadenylation signal or both. 3' control elements can also include control elements connecting to coding regions. For example, it is possible to express multiple LAMP-2 isoforms under the control of a single promoter by placing an internal ribosome entry site (IRES) (see for example FIGS. 1I and 1M) or a self-cleaving peptide sequence (such as a picornaviral 2A peptide; see for example FIGS. 1J and 1N) between the 1st and 2nd, and 2nd and 3rd (if present) isoforms. In the case of an IRES, 2 or 3 polypeptides are translated. In the case of a self-cleaving peptide the LAMP-2 isoforms along with the intervening self-cleaving peptide are present in the vector as a single reading frame that is translated as a single polypeptide that is cleaved into it substituent LAMP-2 isoforms after or during translation.

Transcription under control of a single promoter is also achievable when the vector is constructed to support alternative splicing. In such constructs the first eight exons of LAMP-2 are present as spliced together in cDNA followed by two or three intron-exon pairs to include two or all three of the alternative exons that give rise to the three LAMP-2 isoforms (see for example FIGS. 1K and 1O). In various embodiments intron-exon pairs occur in any order, either mirroring the natural order of B, A, C, or altering it. The native introns are too long to include in vectors that are size constrained such as AAV. In such cases the introns are truncated by removal of central sequences while retaining the necessary 5' and 3' splice sites and splice signals. Typically, retention of just a few bases at the 5' end of the intron and about 100-200 bases at the 3' end of the intron is sufficient to ensure splicing. Alternatively, heterologous introns can be substituted for the native introns.

The AAV expression vector which harbors the DNA molecule of interest bounded by AAV ITRs, can be constructed by directly inserting the selected sequence (s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g. U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin, 1994; Shelling and Smith, 1994; and Zhou et al., 1994, the complete contents of each of which is hereby incorporated by reference.

Alternatively, AAV ITRs can be excised from the viral genome or from an AAV vector containing the same and fused 5' and 3' of a selected nucleic acid construct that is present in another vector using standard ligation techniques. AAV vectors which contain ITRs have been described in, e.g. U.S. Pat. No. 5,139,941, the complete contents of which is hereby incorporated by reference. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. See, e.g., Edge Nature, vol, 292, 1981, page 756; Nambair et al., Science, vol. 223, 1984, page 1299; Jay et al., J. Biol. Chem. vol. 259, 1984, page 6311, the complete contents of each of which is hereby incorporated by reference. In order to produce AAV virions, an AAV expression vector is introduced into a suitable host cell using known techniques, such as by transfection. A number of transfection techniques are generally known in the art. See, e.g. Graham et al, Virology, 52, 456-467, (1973); Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al., 1973), direct microinjection into cultured cells (Capeechi, 1980), electroporation (Shigekawa et al., 1988), liposome mediated gene transfer (Mannino et al., 1988), lipid-mediated transduction (Feigner et al., 1987, PNAS USA, 84, 21, 7413-17), and nucleic acid delivery using high-velocity microprojectiles (Klein et al., 1987, Endocrinology 120:2339-45). The complete contents of each of the foregoing references are hereby incorporated by reference in entirety.

In one embodiment, the AAV, comprises, in addition to a LAMP-2 isoform encoding nucleic acid sequence(s), the backbone of AAV vector with ITR derived from AAV2, the promoter, such as the mouse PGK (phosphoglycerate kinase) gene or the cytomegalovirus/chicken beta-actin hybrid promoter (CAG) consisting of the enhancer from the cytomegalovirus immediate gene and the promoter, splice donor, and intron from the chicken beta-actin gene, the splice acceptor from rabbit β-globin, or any promoter such as PGK, CAG, MCK, EF-1 or native LAMP-2 promoter. In varying embodiments, the viral vector is encapsulated with an anionic liposome, e.g., as described in U.S. Patent Publ. No. 2015/0284691.

In varying embodiments structure of the expression cassette within the vector comprises first and second (e.g., 5' and 3') inverse terminal repeats (ITRs) from any known AAV serotype or subgroup including scAAV, any known promoter region (e.g., a cytomegalovirus (CMV) promoter or a chicken-beta actin promoter) with or without any known enhancer element (e.g., a CMV enhancer), the lysosome-associated protein 2 gene (including all known isoforms, e.g., LAMP-2A, LAMP-2B, and LAMP-2C, and all known polymorphisms of those isoforms), and a polyadenylation signal (including, but not limited to, rabbit beta-globin or).

Translation of the virally delivered LAMP-2 isoform gene, or a combination of various isoform genes, results in expression of the LAMP-2 protein for that particular isoform, which is then targeted to the lysosomal membranes of the host cell by the host cell machinery. Restoration of LAMP-2 isoform(s) expression and function then restores autophagic flux (potentially including, but not necessarily limited to, all known forms of autophagy such as macroautophagy, mitophagy, chaperone-mediated autophagy, and DNA/RNA autophagy), which is deficient and causal in Danon patients, allowing diseased host cells to eliminate toxic cellular components and damaged organelles and thus improving cell function and survival. Ultimately, restoration of LAMP-2 isoform(s) expression serves to treat the underlying genetic deficiency that causes Danon disease and relieves the phenotype and symptoms of the disease. In other disorders of autophagy where LAMP-2 may be expressed, but not at a sufficient level to create adequate autophagic flux and thus promote normal cell function and survival, delivery of the transgenic LAMP-2 isoform(s) by the rAAV vector results in overexpression of the resultant LAMP-2 protein(s). This overexpression restores autophagic flux to near normal, normal or supra-normal levels. Restoration of autophagic flux in diseases that cause a disruption of normal autophagy then alleviates, mitigates, and/or reverses the disease phenotype and symptoms.

4. Vector Pharmaceutical Compositions

Provided are pharmaceutical compositions, e.g., for use in preventing or treating a disorder characterized by deficient autophagic flux (e.g., Danon disease) which comprises a therapeutically effective amount of a vector which comprises a nucleic acid sequence of a polynucleotide that encodes one or more isoforms of LAMP-2.

It will be understood that the single dosage or the total daily dosage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific nucleic acid or polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range per adult per day. The therapeutically effective amount of the vector according to the invention that should be administered, as well as the dosage for the treatment of a pathological condition with the number of viral or non-viral particles and/or pharmaceutical compositions described herein, will depend on numerous factors, including the age and condition of the patient, the severity of the disturbance or disorder, the method and frequency of administration and the particular peptide to be used.

The pharmaceutical compositions that contain the vector may be in any form that is suitable for the selected mode of administration, for example, for intraventricular, intramyocardarial, intracoronary, intravenous, intra-arterial, intrarenal, intraurethral, epidural or intramuscular administration. The gene therapy vector comprising a polynucleotide encoding one or more LAMP-2 isoforms can be administered, as sole active agent, or in combination with other active agents, in a unit administration form, as a mixture with conventional pharmaceutical supports, to animals and human beings.

In varying embodiments, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid. It must be stable under the conditions of manufacture and storage and must be preserved against the contaminating action of microorganisms, such as bacteria and fungi.

Solutions comprising the gene therapy vectors as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The gene therapy vectors can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be as solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

5. Methods of Treating Diseases of Autophagy

Further provided are methods of preventing, mitigating, ameliorating, reducing, inhibiting, eliminating and/or reversing one or more symptoms of Danon disease or another autophagy disorder in a subject in need thereof, comprising administering to the subject a gene therapy vector as described above and herein, e.g., an adeno-associated virus (AAV) vector comprising an expression cassette comprising a polynucleotide encoding one or more isoforms of lysosome-associated membrane protein 2 (LAMP-2). The vector is delivered to the subject in need thereof and whereby the polynucleotide encoding one or more LAMP-2 isoforms is expressed by the transduced cells at a therapeutically effective level.

In one particular embodiment, the vector is an AAV9. In another particular embodiment the vector is an AAV8. In another particular embodiment, the vector is an AAVrH10. In a further aspect of these embodiments, they are used specifically in the treatment of Danon disease.

In varying embodiments, the vector is administered via a route selected from the group consisting of intravenous, intraarterial, intracardiac, intracoronary, intramyocardial, intrarenal, intra-urethral, epidural, subcutaneous, and intramuscular. In varying embodiments, the vector is delivered directly into the myocardium by epicardiac injection via a minithoracotomy, by intracoronary injection, by endomyocardic injection or by another type of injection useful in the heart. Additional routes of administration may also comprise local application of the vector under direct visualization, e.g., superficial cortical application, or other nonstereotactic application.

Viral vectors will typically provoke an immune response which can include an antibody response that can reduce or completely inhibit the effectiveness of a particular vector in that individual when repeat dosing becomes necessary or desirable. Repeat dosing may become appropriate, for example, because vector can be lost over time due to cell proliferation, especially episomal vectors. Tissues that are more difficult to access can require multiple administrations of vector to transfect a sufficient number of cells for effective treatment of the disease. Expression of the transgene can also be lost over time. The need to administer a gene therapy vector in the face of an inhibiting antibody response can be addressed in various ways. For example, antibody titers can be reduced by apheresis prior to administration of the vector or the patient can be immunosuppressed with an appropriate medical regimen. Alternatively, empty AAV capsid could be administered to bind host antibodies and immune cells prior to injection of therapeutic AAV containing the LAMP-2 transgene(s). Depending on the target tissue, a direct local administration instead of a systemic administration can be useful in overcoming or ameliorating the inhibitory effect of anti-vector antibodies. In yet another approach, a vector based on a different serotype of the virus from which it was derived can be used. For example, if an AAV9 vector was used initially and there becomes a problem with anti-AAV antibody titer, but there is need for further gene therapy, one can administer an AAV8 vector carrying the same (or different) gene construct.

Upon formulation, solutions can be administered in a manner compatible with the dosage formulation and in such amount as is therapeutically effective. The formulations are easily administered in a variety of dosage forms, such as the type of injectable solutions described above, but drug release capsules and the like can also be employed. Multiple doses can also be administered.

As appropriate, the vectors described herein may be formulated in any suitable vehicle for delivery. For instance, they may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but are not limited to water, alcoholic/aqueous solutions, emulsions or suspensions, including saline and buffered media. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes.

An appropriate regimen can be determined by a physician, and will depend on the age, sex, weight, of the subject, and the stage of the disease. As an example, for delivery of a nucleic acid sequence encoding a LAMP-2 polypeptide using a viral expression vector, each unit dosage of LAMP-2 polypeptide expressing vector may comprise 2.5 µl to 100 µl of a composition including a viral expression vector in a pharmaceutically acceptable fluid at a concentration ranging from $10^{11}$ to $10^{16}$ viral genome per ml, for example.

In some regimens, a vector carrying a gene for a single LAMP-2 isoform is used, for example LAMP-2B. In other regimens, a vector carrying a gene for two LAMP-2 isoforms is used, for example LAMP-2B and LAMP-2A. In some embodiments, the two isoforms are carried in different vectors preparations. In one aspect, both vector preparations are derived from the same vector, for example an AAV9 vector or any other particular vector described above. In other embodiments, both polypeptides are encoded in a single vector; see for example FIG. 1. Similarly, if the regimen comprises administration of nucleic acid sequences encoding all three isoforms, the isoforms can be carried in individual vectors or in a single vector. In regimens using multiple isoforms carried by individual vectors the multiple vectors can be administered at the same time, individually or mixed together, or they can be administered sequentially at intervals of hours, days, or weeks.

6. Kits

Further provided are kits comprising a gene therapy vector comprising a polynucleotide encoding one or more LAMP-2 isoforms, as described above and herein. In varying embodiments, the kits provide the gene therapy vectors prepared in one or more unitary dosage forms ready for administration to a subject, for example in a preloaded syringe or in an ampoule. In varying embodiments, the gene therapy vector is provided in a lyophilized form.

EXAMPLES

Example 1

AAV9 Gene Therapy

Particular vectors, consistent with the descriptions above, were constructed as an AAV9 vector with ITRs derived from AAV2 and encoding either LAMP-2A or LAMP-2B under the control of a chicken beta-actin promoter with a CMV enhancer (CAG promoter). Additionally, these vectors incorporated the woodchuck hepatitis virus posttranscriptional regulatory element and rabbit beta-globin polyadenylation signal (see FIG. 1B). These vectors were obtained from the National Heart, Lung, and Blood Institute Gene Therapy Resource Program Preclinical Vector Core facility at the University of Pennsylvania. The human LAMP-2 sequences were incorporated with the expectation that they would be functional in mouse due to the high degree of sequence identity between the homologues especially at the C-terminal region, which forms the transmembrane and cytoplasmic tail components of the protein (see FIG. 4).

The vector is used to deliver the LAMP-2 isoforms in vivo. The AAV9 serotype has excellent tropism for cardiac and skeletal muscle as well as nervous tissue, the organs most affected by Danon disease. However, Danon is a multi-system disorder and many different organs can potentially be involved; therefore, expression of the transgenic LAMP-2 isoforms is under the control of a constitutively active chicken beta-actin (CBA) promoter with a cytomegalovirus (CMV) enhancer (CAG construct). This promoter is ubiquitously active and will allow for LAMP-2 transgene expression in all tissues depending on infection efficiency. An AAV9 vector carrying an enhanced green fluorescent protein (eGFP) gene was also obtained for use as a control reagent.

Example 2

Administration of AAV9 LAMP-2 Isoform Vectors to LAMP-2 Knock Out Mice

Lamp-2 KO mice (*Nature*. 2000 Aug. 24; 406(6798):902-6; *Basic Res Cardiol*. 2006 July; 101(4):281-91) develop a Danon-like syndrome, though the severity of disease is more moderate than the human disease, likely at least in part due to the shorter life span of mice providing less time for damage due to impaired autophagic flux to accumulate. It is therefore desirable to wait until the mice are at least 3 months old and preferably 5-6 months old before initiating treatment so that there has been sufficient accumulation of pathology that its reversal is readily detectable.

In an idealized procedure, six-month old Lamp-2 KO mice and receive $5 \times 10^{11}$, $1 \times 10^{12}$, or $2 \times 10^{12}$ genome copies (gc) of AAV vector via intravenous injection into the external jugular vein. In various experiments, WT mice receive the LAMP-2 isoform vectors and Lamp-2 KO mice receive eGFP vector as controls. Sufficient numbers of mice are used so that subpopulations can be sacrificed and evaluated at various time points, for example, at 1, 2, and 6 months post-administration.

Example 3

Figure 5A:
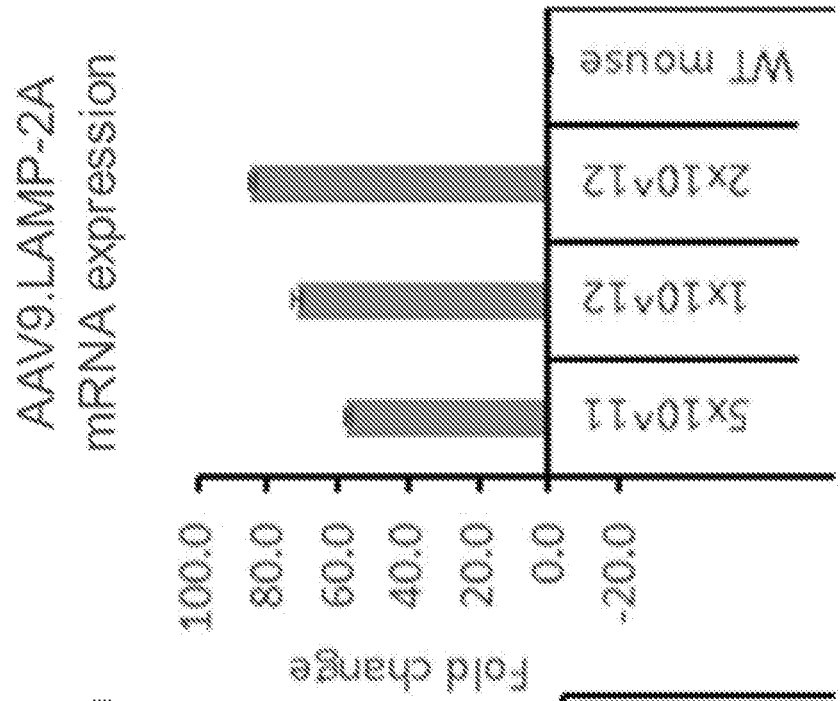
FIG. 5A-B illustrates the dose dependent increase in LAMP-2B (FIG. 5A) and LAMP-2A (FIG. 5B) mRNA expression following administration of AAV9 vectors carrying those genes.
Figure 5B:
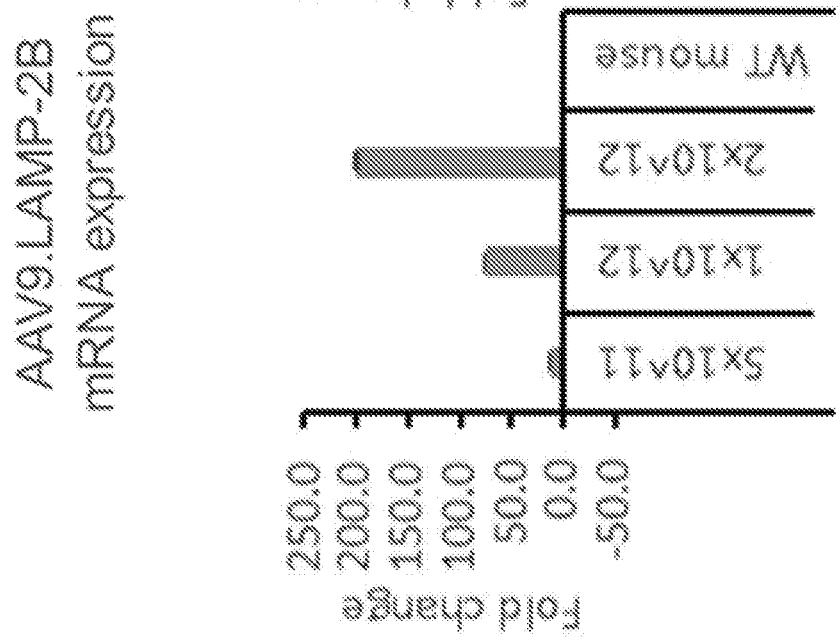

Evaluation of LAMP-2 Isoform Gene Transcription Following Vector Administration Lamp-2 KO mice, approximately 3-4 month of age, received increasing doses of the vectors AAV9.LAMP-2B and AAV9.LAMP-2A (see FIG. 1B and descriptions above) at $5 \times 10^{11}$, $1 \times 10^{12}$, and $2 \times 10^{12}$ gc/mouse. One mouse per condition was sacrificed and RT-qPCR was performed, in triplicate, on digested heart tissue to assess mRNA expression (gene transcription) of the human transgenes. An untreated WT mouse was used to demonstrate no expression of the human LAMP-2 isoforms. The data show a dose-dependent increase in expression of the human transgenes (see FIG. 5).

Example 4

Figure 6:
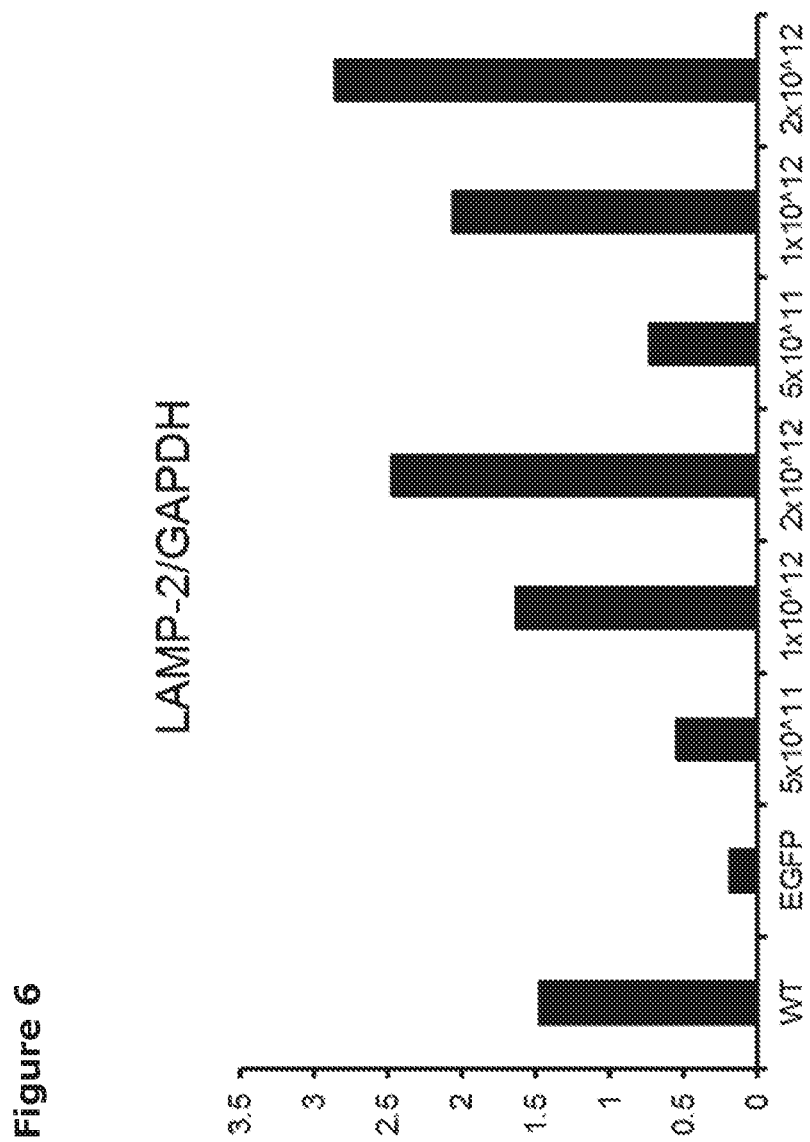
FIG. 6 illustrates the dose dependent increase in LAMP-2B and LAMP-2A protein expression following administration of AAV9 vectors carrying those genes.

Evaluation of LAMP-2 Isoform Protein Expression Following Vector Administration Using the same mice as in Example 3, immunoblotting was performed on digested heart tissue to assess protein expression of the human transgenes relative to GAPDH. A control Lamp-2 KO mouse treated with AAV9.EGFP demonstrated no significant LAMP-2 protein expression. The data show a dose-dependent increase in expression of the human transgenes in mice receiving the viral vectors (see FIG. 6).

Example 5

Figure 7C:
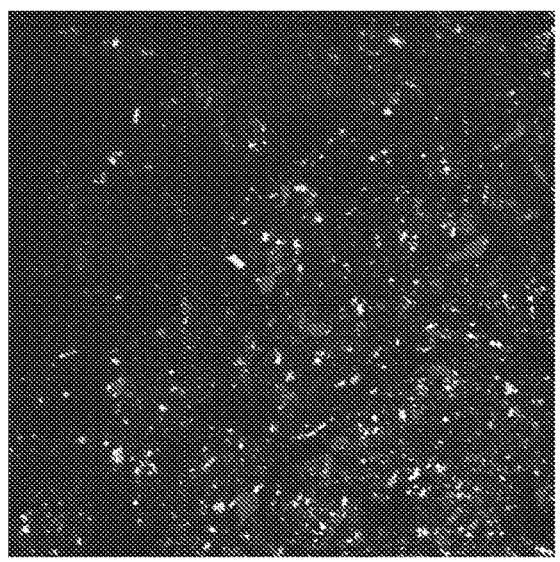
FIG. 7A-C shows fluorescent micrographs of heart sections stained with DAPI (blue) and fluorescently-tagged anti-LAMP-2 antibody (white).
Figure 7B:
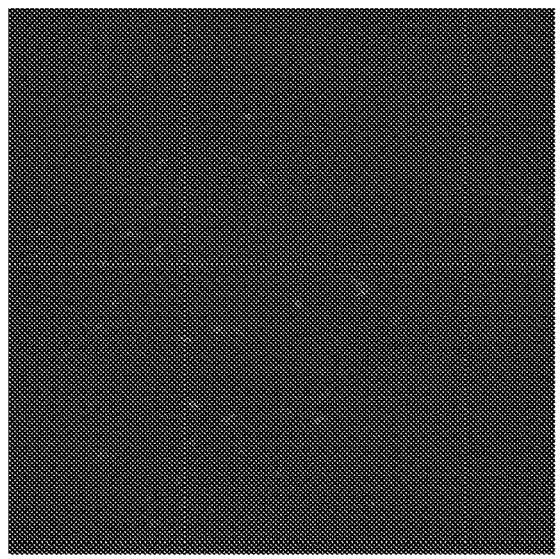
Figure 7A:
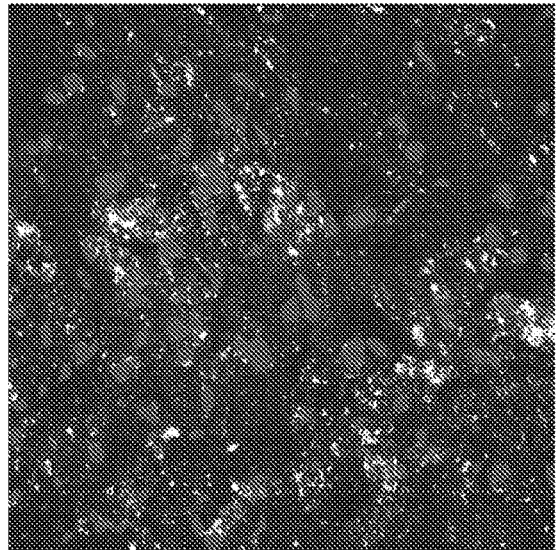

Subcellular Localization of Transgenic LAMP-2B Following Vector Administration Heart sections from a Lamp-2 KO mouse that had received $2 \times 10^{12}$ gc/mouse of either AAV9.LAMP-2B or AAV9.EGFP sacrificed 1 month post-delivery were stained with DAPI (which binds to AT-rich DNA and thus makes cell nuclei visible) and fluorescently-tagged anti-LAMP-2 antibody (see FIG. 7). The pattern of LAMP-2 staining indicates localization of the human transgenic LAMP-2B protein to intracellular vacuoles and is similar to the staining seen in a WT mouse control for the mouse Lamp-2 protein. No human LAMP-2 staining is seen in the Lamp-2 KO mouse receiving the AAV9.EGFP vector control. These data demonstrate that treatment with the AAV9.LAMP-2B vector leads to expression of the human LAMP-2B protein in a physiologically appropriate location.

Figure 8B:
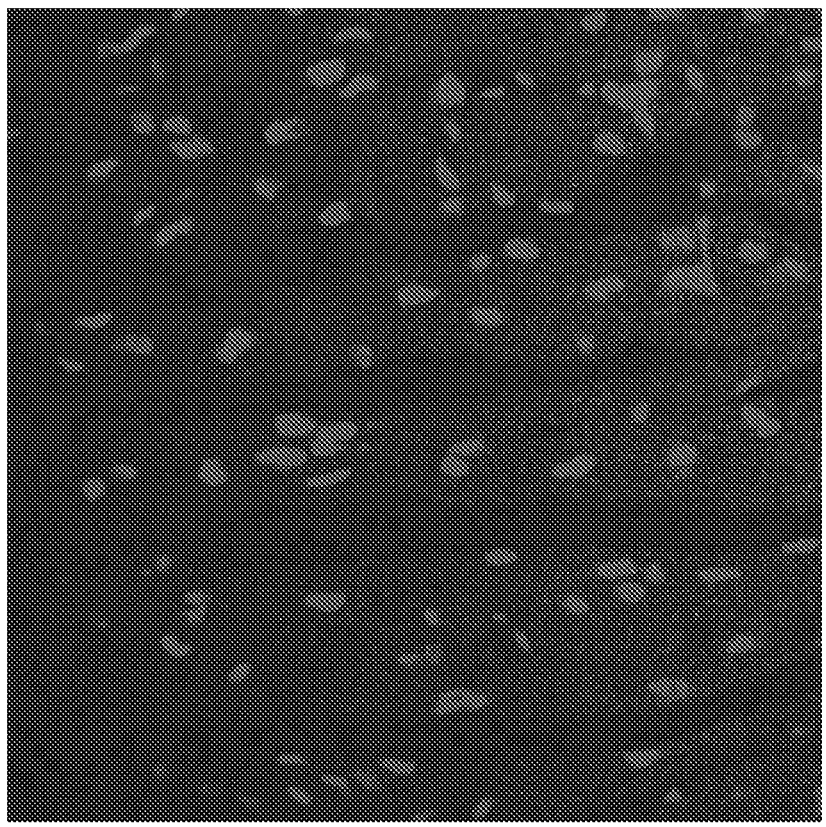
FIG. 8A-B shows fluorescent micrographs of heart sections stained with DAPI (blue) and fluorescently-tagged anti-LAMP-2 antibody (white; some examples highlighted with arrows).
Figure 8A:
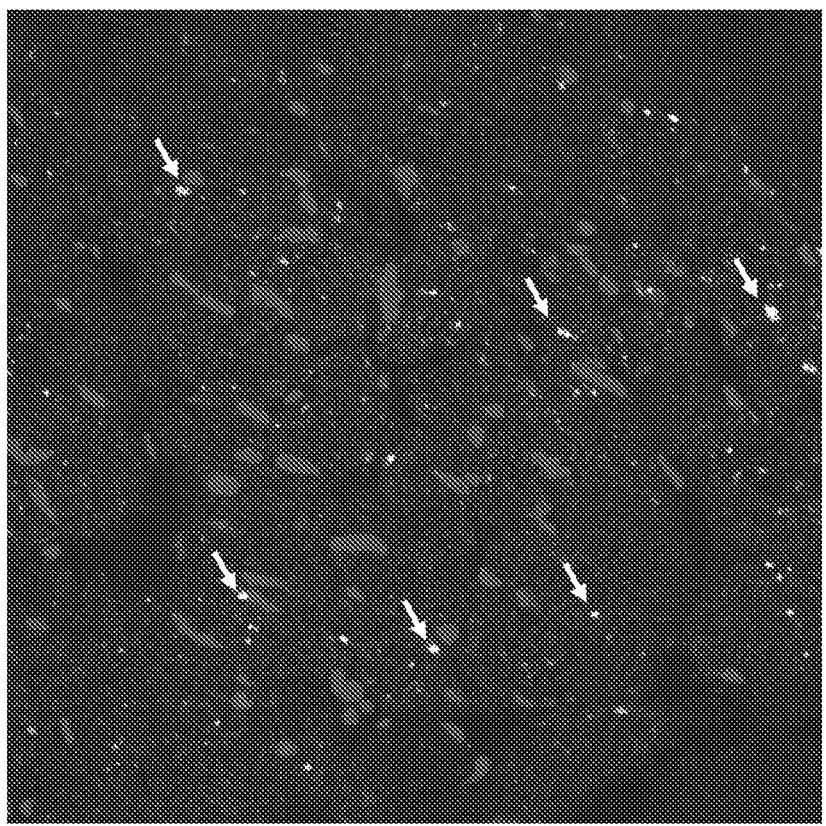

In a similar, experiment human LAMP-2 staining was maintained at 2 months post-delivery of AAV9.LAMP-2B at a dose of $5 \times 10^{11}$ gc/mouse in a test mouse. Though consistent with Example 4, less staining was seen with this lower vector dosage. By comparison, 3 months post-delivery of $5 \times 10^{11}$ gc/mouse of the AAV9.EGFP vector revealed no human LAMP-2 staining. See FIG. 8.

Example 6

The CAG-RFP-EGFP-LC3B Autophagy Reporter System

Figure 9A:
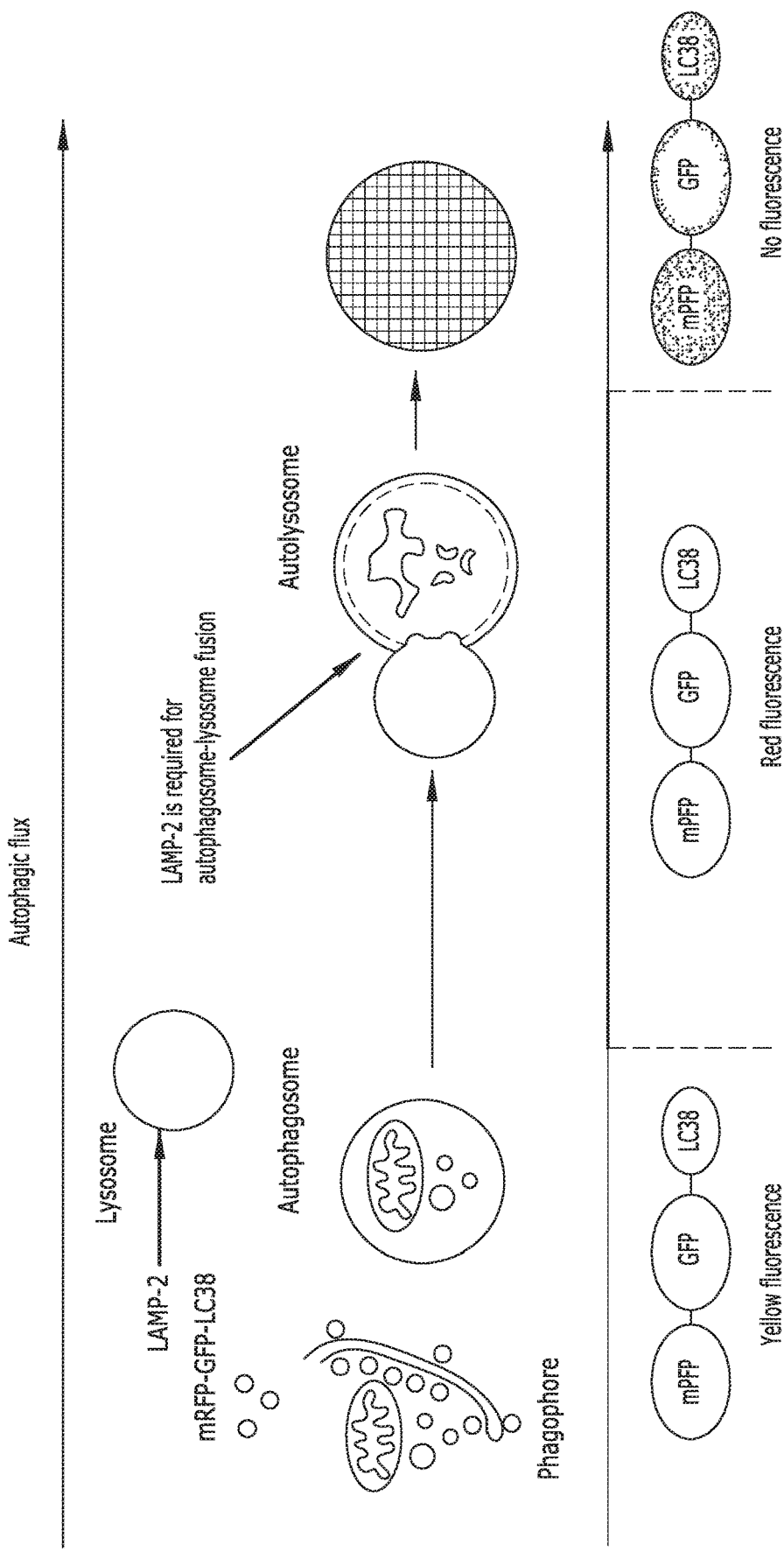
Figure 9H:
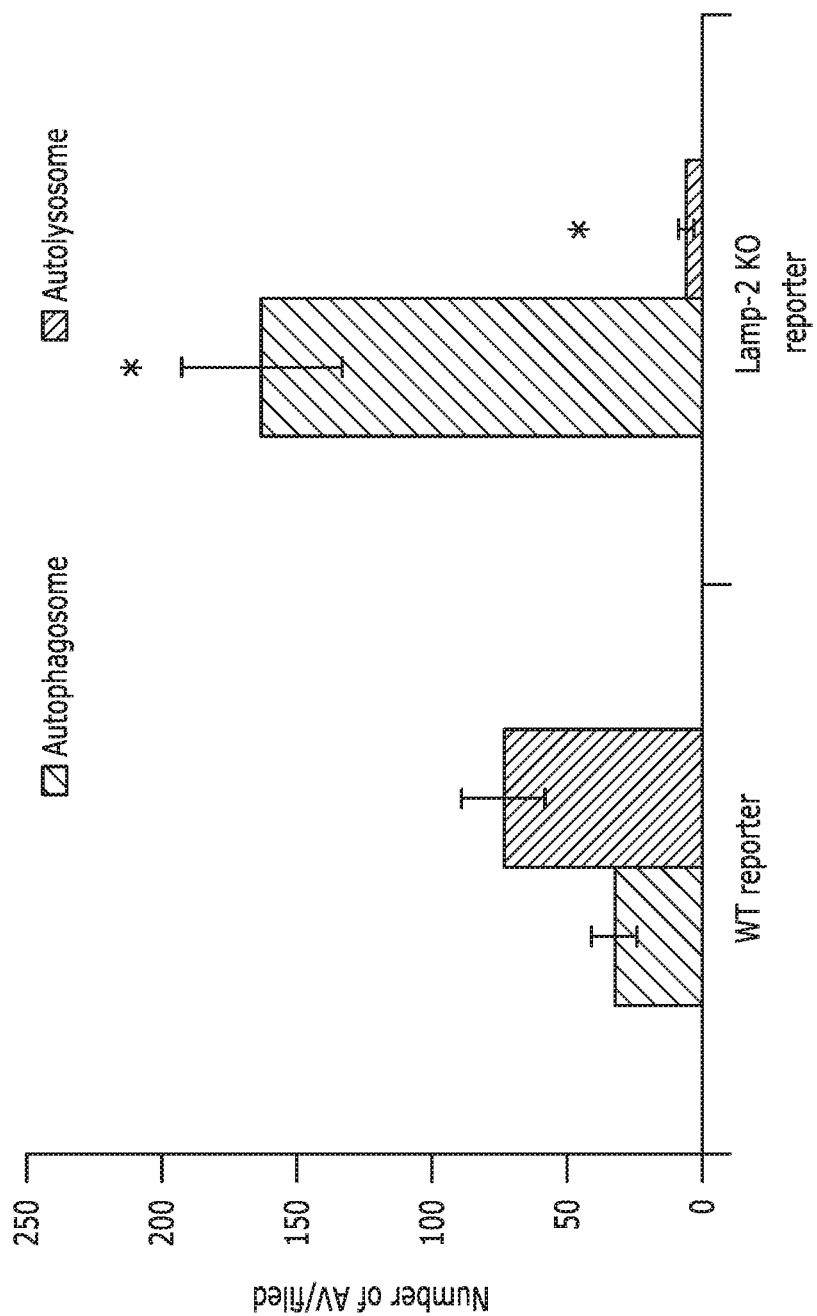

The CAG-RFP-EGFP-LC3B Autophagy Reporter System allows assessment of macroautophagic flux. Microtubule-associated protein 1 light chain 3 (LC3), is expressed on the surface of autophagosomes. A gene fusion is constructed to express LC3 fused to both red fluorescent protein (RFP) and eGFP. When this fused protein is expressed the, RFP component fluoresces in both autophagosomes and lysosomes whereas the eGFP component fluoresces in autophagosomes, but is quenched by the acidic environment of the lysosomes. As a result, in a merged image autophagosomes are yellow and lysosomes are red (see FIG. 9A). When expressed in a WT background, one sees more red puncta than green puncta in separate red and green images and a mixture of red and yellow puncta in merged images (see FIGS. 9B-D'). Lamp-2 is required for normal fusion of autophagosomes with lysosomes to form autolysosomes. Thus, when this construct is expressed in a Lamp-2 KO mouse approximately equal numbers of red and green puncta are seen in separate red and green images with almost entirely yellow puncta in the merged images (see FIGS. 9E-G'). The accumulation of autophagosomes and near absence of autolysosomes, along with an overall greater number of autophagic vacuoles (AVs), reflects a defect in autophagic flux due to the absence of Lamp-2 (see FIG. 9H).

Example 7

Figure 10E:
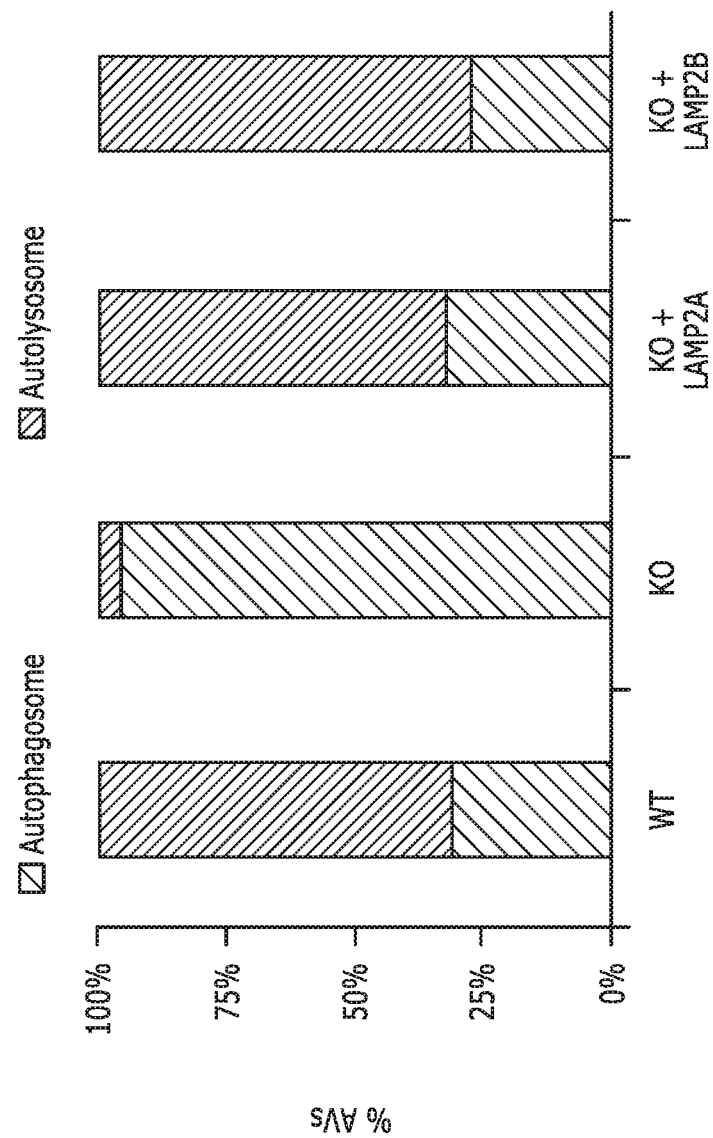

Administration of Vector Carrying Either LAMP-2A or LAMP-2B Restores Autophagic Flux Lamp-2 KO mice expressing the CAG-RFP-EGFP-LC3B construct (Lamp-2 KO/CAG-RFP-EGFP-LC3B reporter mice) were administered either AAV9.LAMP-2B or AAV9.LAMP-2A and compared to Lamp-2 KO mice expressing the CAG-RFP-EGFP-LC3B autophagy reporter system (CAG-RFP-EGFP-LC3B reporter mice). One month post vector delivery, the mice were sacrificed and heart sections assessed by fluorescent microscopy to assess autophagic flux. The untreated Lamp-2 KO/reporter mice continued to show almost only yellow autophagic vacuoles, that is autophagosomes (see FIG. 10B and FIG. 9G'). In contrast, the Lamp-2 KO/reporter mice receiving either gene therapy vector, AAV9.LAMP-2B or AAV9.LAMP-2A, showed many red autophagic vacuoles, that is autolysosomes, in a similar proportion to a control WT reporter mouse (see FIGS. 10A, C and D and exemplary puncta therein indicated with arrows). Quantitation of AVs demonstrated that the proportion of immature autophagosomes to mature autolysosomes was similar in treated Lamp-2 KO mice compared to WT mice (see FIG. 10E). Thus, gene therapy with either AAV9.LAMP-2B or AAV9.LAMP-2A restored normal autophagosome-lysosome fusion in the cardiomyocytes of Lamp-2 KO mice.

Example 8

Restoration of Cardiomyocyte Ultrastructure as Assessed by Electron Microscopy

A Lamp-2 KO mouse was injected intravenously with $5 \times 10^{11}$ gc/mouse of AAV9.LAMP-2B and compared to an age-matched historical Lamp-2 KO mouse and a WT mouse that were not treated. One month post vector delivery the mice were sacrificed and heart sections analyzed by electron microscopy. As compared to WT (see FIGS. 11A, A'), the untreated Lamp-2 KO mouse showed an accumulation and increase in size of AVs (see FIGS. 11B, B', yellow arrows) and an increase in the number of abnormal mitochondria (see FIG. 11B, red arrows). In contrast, electron micrographs of the Lamp-2 KO mouse treated with AAV9.LAMP-2B more closely resembled the ultrastructure of the untreated WT mouse (see FIGS. 11C, C'). Thus, treatment with the gene therapy vector restores the ultrastructure of cardiomyocytes.

In summary, these examples show that gene therapy vectors based on adeno-associated virus encoding the LAMP-2A and LAMP-2B isoforms can be administered intravenously to successfully achieve transgene expression in heart tissue. Additionally, such expression leads to the reversal of defects in autophagic flux and cardiomyocyte ultrastructure, defects that are also associated with Danon disease. These data support the use of such vectors for gene therapy in the treatment of Danon disease and other disorders related to defects in autophagic flux.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A serotype 9 adeno-associated virus (AAV9) vector comprising a polynucleotide encoding lysosome-associated membrane protein 2B (LAMP-2B) operatively linked to a hybrid promoter comprising a chicken beta-actin promoter and a CMV enhancer (CAG promoter).

2. The vector of claim 1, wherein the expression cassette comprises operably linked in the 5' to 3' direction, a first inverse terminal repeat, the CAG promoter, the polynucleotide encoding LAMP-2B, a 3' untranslated region including a polyadenylation signal, and a second inverse terminal repeat.

3. The vector of claim 1, wherein the LAMP-2B is human LAMP-2B.

4. The vector of claim 1, wherein the polynucleotide encoding LAMP-2B has at least about 90% sequence identity to the nucleic acid sequence of SEQ ID NO:2.

5. The gene therapy vector of claim 4, wherein the polynucleotide encoding LAMP-2B comprises the nucleic acid sequence of SEQ ID NO:2.

6. A method of treating impaired autophagic flux in a mammal that has Danon disease, the method comprising:

intravenously administering an adeno-associated virus 9 (AAV9) vector to the mammal that has impaired autophagic flux, a mutation in a lysosomal-associated protein 2 (LAMP2) gene, and Danon disease;

wherein the AAV9 vector comprises a polynucleotide encoding lysosome-associated membrane protein 2B (LAMP-2B) operatively linked to a hybrid promoter comprising a chicken beta-actin promoter and a CMV enhancer (CAG promoter) such that the impaired autophagic flux is improved.

7. The method of claim 6, wherein the vector is administered to the mammal multiple times.

8. The method of claim 6, wherein the mammal has reduced or non-detectable LAMP-2B expression.

9. The method of claim 6, wherein the AAV9 vector comprises operably linked in the 5' to 3' direction, a first inverse terminal repeat, the CAG promoter, the polynucleotide encoding LAMP-2B, a 3' untranslated region including a polyadenylation signal, and a second inverse terminal repeat.

10. The method of claim 6, wherein the LAMP-2B is human LAMP-2B.

11. The method of claim 6, wherein the polynucleotide encoding LAMP-2B has at least about 90% sequence identity to the nucleic acid sequence of SEQ ID NO:2.

12. The method of claim 6, wherein the polynucleotide encoding LAMP-2B comprises the nucleic acid sequence of SEQ ID NO:2.

13. The method of claim 12, wherein the vector is administered to the mammal multiple times.

14. The method of claim 12, wherein the mammal has reduced or non-detectable LAMP-2B expression.

* * * * *

SEQUENCE LISTING

```
<160> NUMBER OF SEQ ID NOS: 12

<210> SEQ ID NO 1
<211> LENGTH: 1233
<212> TYPE: DNA
<213> ORGANISM: Homo sapiens

<400> SEQUENCE: 1
atggtgtgct tccgcctctt cccggttccg ggctcagggc tcgttctggt ctgcctagtc      60
ctgggagctg tgcggtctta tgcattggaa cttaatttga cagattcaga aaatgccact     120
tgcctttatg caaaatggca gatgaatttc acagttcgct atgaaactac aaataaaact     180
tataaaactg taaccatttc agaccatggc actgtgacat ataatggaag catttgtggg     240
gatgatcaga atggtcccaa aatagcagtg cagttcggac ctggcttttc ctggattgcg     300
aattttacca aggcagcatc tacttattca attgacagcg tctcattttc ctacaacact     360
ggtgataaca caacatttcc tgatgctgaa gataaggaa ttcttactgt tgatgaactt     420
ttggccatca gaattccatt gaatgacctt tttagatgca atagtttatc aactttggaa     480
aagaatgatg ttgtccaaca ctactgggat gttcttgtac aagcttttgt ccaaaatggc     540
acagtgagca caaatgagtt cctgtgtgat aaagacaaaa cttcaacagt ggcacccacc     600
atacacacca ctgtgccatc tcctactaca cacctactc caaaggaaaa accagaagct     660
ggaacctatt cagttaataa tggcaatgat acttgtctgc tggctaccat ggggctgcag     720
ctgaacatca ctcaggataa ggttgcttca gttattaaca tcaaccccaa tacaactcac     780
tccacaggca gctgccgttc tcacactgct ctacttagac tcaatagcag caccattaag     840
tatctagact ttgtctttgc tgtgaaaaat gaaaaccgat tttatctgaa ggaagtgaac     900
atcagcatgt atttggttaa tggctccgtt ttcagcattg caaataacaa tctcagctac     960
```

```
tgggatgccc ccctgggaag ttcttatatg tgcaacaaag agcagactgt ttcagtgtct    1020
ggagcatttc agataaatac ctttgatcta agggttcagc ctttcaatgt gacacaagga    1080
aagtattcta cagctcaaga ctgcagtgca gatgacgaca acttcctagt gcccatagcg    1140
gtgggagctg ccttggcagg agtacttatt ctagtgttgc tggcttattt tattggtctc    1200
aagcaccatc atgctggata tgagcaattt tag                                 1233

<210> SEQ ID NO 2
<211> LENGTH: 1233
<212> TYPE: DNA
<213> ORGANISM: Homo sapiens

<400> SEQUENCE: 2
atggtgtgct tccgcctctt cccggttccg ggctcagggc tcgttctggt ctgcctagtc      60
ctgggagctg tgcggtctta tgcattggaa cttaatttga cagattcaga aaatgccact     120
tgcctttatg caaatggca gatgaatttc acagttcgct atgaaactac aaataaaact     180
tataaaactg taaccatttc agaccatggc actgtgacat ataatggaag catttgtggg    240
gatgatcaga atggtcccaa atagcagtg cagttcggac ctggcttttc ctggattgcg     300
aattttacca aggcagcatc tacttattca attgacagcg tctcattttc ctacaacact    360
ggtgataaca acacatttcc tgatgctgaa gataaaggaa ttcttactgt tgatgaactt    420
ttggccatca gaattccatt gaatgacctt tttagatgca atagtttatc aactttggaa    480
aagaatgatg ttgtccaaca ctactgggat gttcttgtac aagcttttgt ccaaaatggc    540
acagtgagca caaatgagtt cctgtgtgat aaagacaaaa cttcaacagt ggcacccacc    600
atacaccaca ctgtgccatc tcctactaca cacctactc caaaggaaaa accagaagct    660
ggaacctatt cagttaataa tggcaatgat acttgtctgc tggctaccat ggggctgcag    720
ctgaacatca ctcaggataa ggttgcttca gttattaaca tcaaccccaa tacaactcac    780
tccacaggca gctgccgttc tcacactgct ctacttagac tcaatagcag caccattaag    840
tatctagact ttgtctttgc tgtgaaaaat gaaaaccgat tttatctgaa ggaagtgaac    900
atcagcatgt atttggttaa tggctccgtt ttcagcattg caaataacaa tctcagctac    960
tgggatgccc ccctgggaag ttcttatatg tgcaacaaag agcagactgt ttcagtgtct    1020
ggagcatttc agataaatac ctttgatcta agggttcagc ctttcaatgt gacacaagga    1080
aagtattcta cagcccaaga gtgttcgctg gatgatgaca ccattctaat cccaattata    1140
gttggtgctg tctttcagg cttgattatc gttatagtga ttgcttacgt aattggcaga    1200
agaaaaagtt atgctggata tcagactctg taa                                1233

<210> SEQ ID NO 3
<211> LENGTH: 1236
<212> TYPE: DNA
<213> ORGANISM: Homo sapiens

<400> SEQUENCE: 3
atggtgtgct tccgcctctt cccggttccg ggctcagggc tcgttctggt ctgcctagtc     60
ctgggagctg tgcggtctta tgcattggaa cttaatttga cagattcaga aaatgccact    120
tgcctttatg caaatggca gatgaatttc acagttcgct atgaaactac aaataaaact    180
tataaaactg taaccatttc agaccatggc actgtgacat ataatggaag catttgtggg    240
gatgatcaga atggtctcaa aatagcagtg cagttcggac ctggcttttc ctggattgcg    300
```

```
aattttacca aggcagcatc tacttattca attgacagcg tctcattttc ctacaacact    360
ggtgataaca caacatttcc tgatgctgaa gataaaggaa ttcttactgt tgatgaactt    420
ttggccatca gaattccatt gaatgacctt tttagatgca atagtttatc aactttggaa    480
aagaatgatg ttgtccaaca ctactgggat gttcttgtac aagcttttgt ccaaaatggc    540
acagtgagca caaatgagtt cctgtgtgat aaagacaaaa cttcaacagt ggcacccacc    600
atacacacca ctgtgccatc tcctactaca cacctactc caaggaaaa accgaaagct     660 ggaacctatt cagttaataa tggcaatgat acttgtctgc tggctaccat ggggctgcag    720
ctgaacatca ctcaggataa ggttgcttca gttattaaca tcaaccccaa tacaactcac    780
tccacaggca gctgccgttc tcacactgct ctacttagac tcaatagcag caccattaag    840
tatctagact ttgtctttgc tgtgaaaaat gaaaaccgat tttatctgaa ggaagtgaac    900
atcagcatgt atttggttaa tggctccgtt ttcagcattg caaataacaa tctcagctac    960
tgggatgccc ccctgggaag ttcttatatg tgcaacaaag agcagactgt ttcagtgtct   1020
ggagcatttc agataaatac ctttgatcta agggttcagc ctttcaatgt gacacaagga   1080
aagtattcta cagctgaaga atgttctgct gactctgacc tcaactttct tattcctgtt   1140
gcagtgggtg tggccttggg cttccttata attgttgtct ttatctctta tatgattgga   1200
agaaggaaaa gtcgtactgg ttatcagtct gtgtaa                            1236
```

<210> SEQ ID NO 4
<211> LENGTH: 90
<212> TYPE: PRT
<213> ORGANISM: Homo sapiens

<400> SEQUENCE: 4

Trp Asp Ala Pro Leu Gly Ser Ser Tyr Met Cys Asn Lys Glu Gln Thr
1               5                   10                  15

Val Ser Val Ser Gly Ala Phe Gln Ile Asn Thr Phe Asp Leu Arg Val
            20                  25                  30

Gln Pro Phe Asn Val Thr Gln Gly Lys Tyr Ser Thr Ala Gln Asp Cys
        35                  40                  45

Ser Ala Asp Asp Asp Asn Phe Leu Val Pro Ile Ala Val Gly Ala Ala
    50                  55                  60

Leu Ala Gly Val Leu Ile Leu Val Leu Leu Ala Tyr Phe Ile Gly Leu
65                  70                  75                  80

Lys His His His Ala Gly Tyr Glu Gln Phe
                85                  90

<210> SEQ ID NO 5
<211> LENGTH: 90
<212> TYPE: PRT
<213> ORGANISM: Mus musculus

<400> SEQUENCE: 5

Trp Asp Ala Pro Leu Gly Ser Ser Tyr Met Cys Asn Lys Glu Gln Val
1               5                   10                  15

Leu Ser Val Ser Arg Ala Phe Gln Ile Asn Thr Phe Asn Leu Lys Val
            20                  25                  30

Gln Pro Phe Asn Val Thr Lys Gly Gln Tyr Ser Thr Ala Gln Asp Cys
        35                  40                  45

Ser Ala Asp Glu Asp Asn Phe Leu Val Pro Ile Ala Val Gly Ala Ala
    50                  55                  60

Leu Gly Gly Val Leu Ile Leu Val Leu Leu Ala Tyr Phe Ile Gly Leu

```
65                  70                  75                  80
Lys Arg His His Thr Gly Tyr Glu Gln Phe
                85                  90

<210> SEQ ID NO 6
<211> LENGTH: 90
<212> TYPE: PRT
<213> ORGANISM: Homo sapiens

<400> SEQUENCE: 6

Trp Asp Ala Pro Leu Gly Ser Ser Tyr Met Cys Asn Lys Glu Gln Thr
1               5                   10                  15

Val Ser Val Ser Gly Ala Phe Gln Ile Asn Thr Phe Asp Leu Arg Val
                20                  25                  30

Gln Pro Phe Asn Val Thr Gln Gly Lys Tyr Ser Thr Ala Gln Glu Cys
            35                  40                  45

Ser Leu Asp Asp Asp Thr Ile Leu Ile Pro Ile Ile Val Gly Ala Gly
        50                  55                  60

Leu Ser Gly Leu Ile Ile Val Ile Val Ile Ala Tyr Val Ile Gly Arg
65                  70                  75                  80

Arg Lys Ser Tyr Ala Gly Tyr Gln Thr Leu
                85                  90

<210> SEQ ID NO 7
<211> LENGTH: 90
<212> TYPE: PRT
<213> ORGANISM: Mus musculus

<400> SEQUENCE: 7

Trp Asp Ala Pro Leu Gly Ser Ser Tyr Met Cys Asn Lys Glu Gln Val
1               5                   10                  15

Leu Ser Val Ser Arg Ala Phe Gln Ile Asn Thr Phe Asn Leu Lys Val
                20                  25                  30

Gln Pro Phe Asn Val Thr Lys Gly Gln Tyr Ser Thr Ala Gln Glu Cys
            35                  40                  45

Ser Leu Asp Asp Asp Thr Ile Leu Ile Pro Ile Ile Val Gly Ala Gly
        50                  55                  60

Leu Ser Gly Leu Ile Ile Val Ile Val Ile Ala Tyr Leu Ile Gly Arg
65                  70                  75                  80

Arg Lys Thr Tyr Ala Gly Tyr Gln Thr Leu
                85                  90

<210> SEQ ID NO 8
<211> LENGTH: 91
<212> TYPE: PRT
<213> ORGANISM: Homo sapiens

<400> SEQUENCE: 8

Trp Asp Ala Pro Leu Gly Ser Ser Tyr Met Cys Asn Lys Glu Gln Thr
1               5                   10                  15

Val Ser Val Ser Gly Ala Phe Gln Ile Asn Thr Phe Asp Leu Arg Val
                20                  25                  30

Gln Pro Phe Asn Val Thr Gln Gly Lys Tyr Ser Thr Ala Glu Glu Cys
            35                  40                  45

Ser Ala Asp Ser Asp Leu Asn Phe Leu Ile Pro Val Ala Val Gly Val
        50                  55                  60

Ala Leu Gly Phe Leu Ile Ile Val Val Phe Ile Ser Tyr Met Ile Gly
65                  70                  75                  80
```

```
Arg Arg Lys Ser Arg Thr Gly Tyr Gln Ser Val
            85                  90
```

<210> SEQ ID NO 9
<211> LENGTH: 91
<212> TYPE: PRT
<213> ORGANISM: Mus musculus

<400> SEQUENCE: 9

```
Trp Asp Ala Pro Leu Gly Ser Ser Tyr Met Cys Asn Lys Glu Gln Val
1               5                   10                  15

Leu Ser Val Ser Arg Ala Phe Gln Ile Asn Thr Phe Asn Leu Lys Val
            20                  25                  30

Gln Pro Phe Asn Val Thr Lys Gly Gln Tyr Ser Thr Ala Glu Glu Cys
        35                  40                  45

Ala Ala Asp Ser Asp Leu Asn Phe Leu Ile Pro Val Ala Val Gly Val
    50                  55                  60

Ala Leu Gly Phe Leu Ile Ile Ala Val Phe Ile Ser Tyr Met Ile Gly
65                  70                  75                  80

Arg Arg Lys Ser Arg Thr Gly Tyr Gln Ser Val
            85                  90
```

<210> SEQ ID NO 10
<211> LENGTH: 410
<212> TYPE: PRT
<213> ORGANISM: Homo sapiens

<400> SEQUENCE: 10

```
Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
            85                  90                  95

Ser Trp Ile Ala Asn Phe Thr Lys Ala Ala Ser Thr Tyr Ser Ile Asp
        100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
            165                 170                 175

Val Gln Asn Gly Thr Val Ser Thr Asn Glu Phe Leu Cys Asp Lys Asp
        180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220
```

```
Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
            245                 250                 255

Asn Thr Thr His Ser Thr Gly Ser Cys Arg Ser His Thr Ala Leu Leu
        260                 265                 270

Arg Leu Asn Ser Ser Thr Ile Lys Tyr Leu Asp Phe Val Phe Ala Val
    275                 280                 285

Lys Asn Glu Asn Arg Phe Tyr Leu Lys Glu Val Asn Ile Ser Met Tyr
290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410

<210> SEQ ID NO 11
<211> LENGTH: 410
<212> TYPE: PRT
<213> ORGANISM: Homo sapiens

<400> SEQUENCE: 11

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
```

```
                180                 185                 190
Lys Thr Ser Thr Val Ala Pro Thr Ile His Thr Thr Val Pro Ser Pro
                195                 200                 205

Thr Thr Thr Pro Thr Pro Lys Glu Lys Pro Glu Ala Gly Thr Tyr Ser
            210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
            275                 280                 285

Lys Asn Glu Asn Arg Phe Tyr Leu Lys Glu Val Asn Ile Ser Met Tyr
            290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
            355                 360                 365

Ser Leu Asp Asp Asp Thr Ile Leu Ile Pro Ile Ile Val Gly Ala Gly
            370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr Leu
                405                 410

<210> SEQ ID NO 12
<211> LENGTH: 411
<212> TYPE: PRT
<213> ORGANISM: Homo sapiens

<400> SEQUENCE: 12

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140
```

```
Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Glu Glu Cys
        355                 360                 365

Ser Ala Asp Ser Asp Leu Asn Phe Leu Ile Pro Val Ala Val Gly Val
    370                 375                 380

Ala Leu Gly Phe Leu Ile Ile Val Val Phe Ile Ser Tyr Met Ile Gly
385                 390                 395                 400

Arg Arg Lys Ser Arg Thr Gly Tyr Gln Ser Val
                405                 410
```